(12) United States Patent
Bach et al.

(10) Patent No.: US 10,124,125 B2
(45) Date of Patent: *Nov. 13, 2018

(54) NEBULIZER

(71) Applicant: Boehringer Ingelheim International GmbH, Ingelheim am Rhein (DE)

(72) Inventors: Alexander Bach, Essen (DE); Jens Besseler, Bingen am Rhein (DE); Holger Holakovsky, Witten (DE); Manuel Daelman, Welver (DE); Gilbert Wuttke, Ingelheim am Rhein (DE)

(73) Assignee: BOEHRINGER INGELHEIM INTERNATIONAL GMBH, Ingelheim am Rhein (DE)

( * ) Notice: Subject to any disclaimer, the term of this patent is extended or adjusted under 35 U.S.C. 154(b) by 859 days.

This patent is subject to a terminal disclaimer.

(21) Appl. No.: 14/591,301

(22) Filed: Jan. 7, 2015

(65) Prior Publication Data

US 2015/0114387 A1 Apr. 30, 2015

Related U.S. Application Data

(63) Continuation of application No. 12/952,488, filed on Nov. 23, 2010, now Pat. No. 8,960,188.

(30) Foreign Application Priority Data

Nov. 25, 2009 (EP) .................................... 09014681

(51) Int. Cl.
*A61M 11/00* (2006.01)
*A61M 15/00* (2006.01)
*B05B 11/00* (2006.01)

(52) U.S. Cl.
CPC ........ *A61M 11/006* (2014.02); *A61M 15/007* (2014.02); *A61M 15/009* (2013.01);
(Continued)

(58) Field of Classification Search
CPC ............ A61M 11/006; A61M 16/0007; A61M 15/0021; A61M 15/0035; A61M 15/0036;
(Continued)

(56) References Cited

U.S. PATENT DOCUMENTS

| | | |
|---|---|---|
| 1,828,864 A | 10/1931 | Hopkins |
| 2,015,970 A | 10/1935 | Schoene |

(Continued)

FOREIGN PATENT DOCUMENTS

| | | |
|---|---|---|
| AU | 2005201364 A1 | 7/2006 |
| CA | 1094549 A | 1/1981 |

(Continued)

OTHER PUBLICATIONS

Abstract in English for JP2002-235940, 2001.
(Continued)

*Primary Examiner* — Gregory Anderson
*Assistant Examiner* — Margaret Luarca
(74) *Attorney, Agent, or Firm* — Matthew B. Dernier, Esq.

(57) ABSTRACT

A nebulizer includes an insertable container and a securing mechanism for holding the container in the nebulizer such that the container can move back and forth but cannot be separated. The securing mechanism is formed by a metal unitary part. The securing mechanism forms a transportation lock for holding the container unmovable in the housing in a delivery state of the nebulizer. The securing mechanism forms a cage which encompasses the container.

23 Claims, 12 Drawing Sheets

Figure 1:
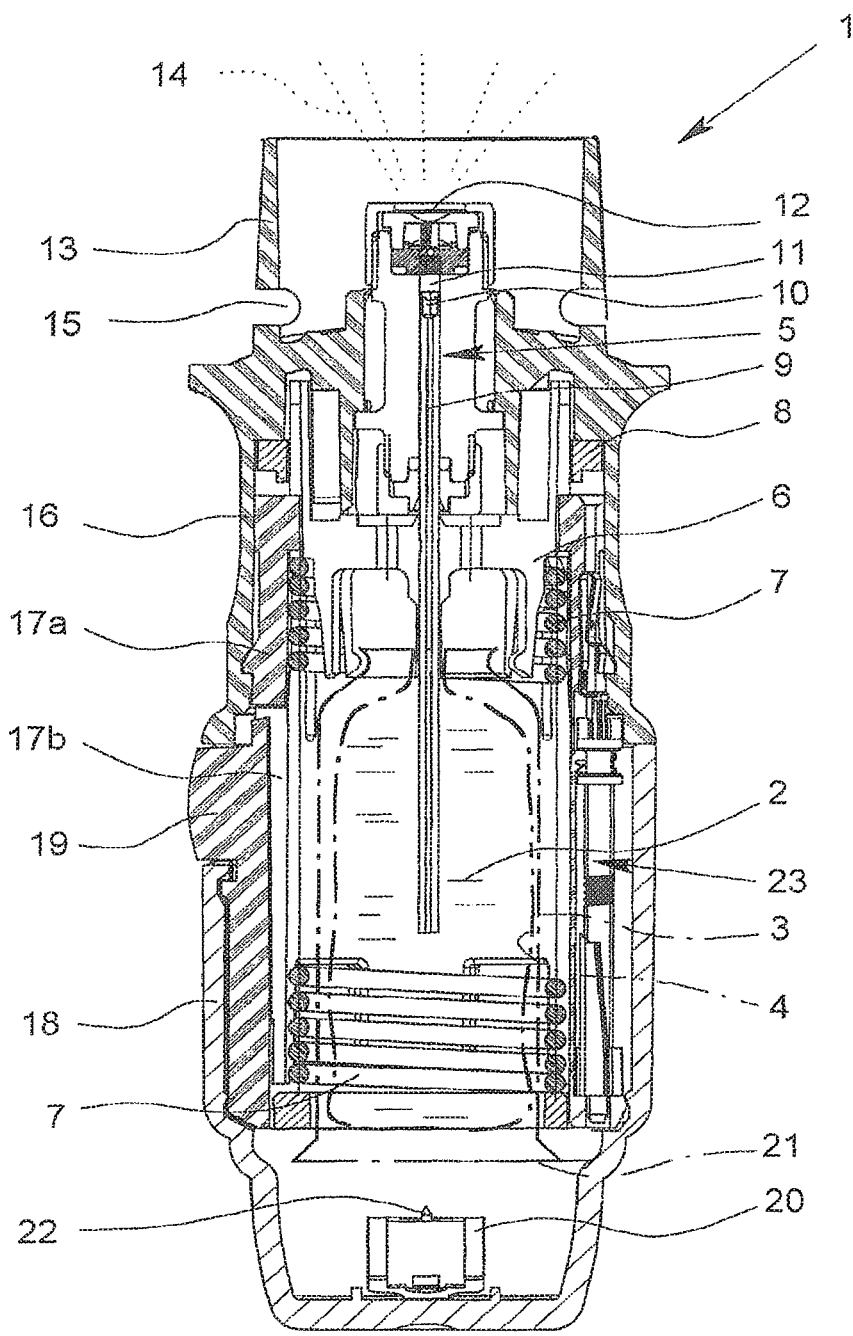

(52) U.S. Cl.
CPC .... *A61M 15/0021* (2014.02); *A61M 15/0035* (2014.02); *A61M 15/0036* (2014.02); *A61M 15/0065* (2013.01); *A61M 15/0081* (2014.02); *A61M 15/0086* (2013.01); *A61M 2205/276* (2013.01); *B05B 11/309* (2013.01)

(58) Field of Classification Search
CPC .......... A61M 15/0065; A61M 15/0081; A61M 15/0086
See application file for complete search history.

(56) References Cited

U.S. PATENT DOCUMENTS

| | | |
|---|---|---|
| 2,127,401 A | 8/1938 | Gillican |
| 2,161,071 A | 6/1939 | McGrath et al. |
| 2,321,428 A | 6/1943 | Schloz |
| 2,329,311 A | 9/1943 | Waters |
| 2,362,103 A | 11/1944 | Smith |
| 2,651,303 A | 9/1953 | Johnson et al. |
| 2,720,969 A | 10/1955 | Kendall |
| 2,793,776 A | 5/1957 | Lipari |
| 2,974,880 A | 3/1961 | Stewart et al. |
| 3,032,823 A | 5/1962 | Sherman et al. |
| 3,157,179 A | 11/1964 | Allen et al. |
| 3,172,568 A | 3/1965 | Modderno |
| 3,196,587 A | 7/1965 | Hayward et al. |
| 3,223,289 A | 12/1965 | Bouet |
| 3,299,603 A | 1/1967 | Shaw |
| 3,348,726 A | 10/1967 | LaCross |
| 3,354,883 A | 11/1967 | Southerland |
| 3,425,591 A | 2/1969 | Pugh |
| 3,440,144 A | 4/1969 | Anderson et al. |
| 3,457,694 A | 7/1969 | Tatibana |
| 3,491,803 A | 1/1970 | Galik |
| 3,502,035 A | 3/1970 | Rene Fedit |
| 3,580,249 A | 5/1971 | Takaoka |
| 3,590,557 A | 7/1971 | Vogel |
| 3,606,106 A | 9/1971 | Yuhas |
| 3,632,743 A | 1/1972 | Geller et al. |
| 3,655,096 A | 4/1972 | Easter |
| 3,674,060 A | 7/1972 | Ruekberg |
| 3,675,825 A | 7/1972 | Morane |
| 3,684,124 A | 8/1972 | Song |
| 3,802,604 A | 4/1974 | Morane et al. |
| 3,817,416 A | 6/1974 | Costa |
| 3,820,698 A | 6/1974 | Franz |
| 3,842,836 A | 10/1974 | Ogle |
| 3,858,580 A | 1/1975 | Ogle |
| 3,861,851 A | 1/1975 | Schiemann |
| 3,870,147 A | 3/1975 | Orth |
| 3,924,741 A | 12/1975 | Kachur et al. |
| 3,933,279 A | 1/1976 | Maier |
| 3,946,732 A | 3/1976 | Hurscham |
| 3,949,751 A | 4/1976 | Birch et al. |
| 3,951,310 A | 4/1976 | Steiman |
| 3,953,995 A | 5/1976 | Haswell et al. |
| 3,973,603 A | 8/1976 | Franz |
| 4,012,472 A | 3/1977 | Lindsey |
| 4,031,892 A | 6/1977 | Hurschman |
| 4,036,439 A | 7/1977 | Green |
| 4,048,997 A | 9/1977 | Raghavachari et al. |
| 4,067,499 A | 1/1978 | Cohen |
| 4,094,317 A | 6/1978 | Wasnich |
| 4,120,995 A | 10/1978 | Phipps et al. |
| 4,126,559 A | 11/1978 | Cooper |
| 4,153,689 A | 5/1979 | Hirai et al. |
| 4,174,035 A | 11/1979 | Wiegner |
| 4,177,938 A | 12/1979 | Brina |
| 4,178,928 A | 12/1979 | Tischlinger |
| 4,195,730 A | 4/1980 | Hunt |
| 4,245,788 A | 1/1981 | Wright |
| 4,275,840 A | 6/1981 | Staar |
| 4,315,570 A | 2/1982 | Silver et al. |
| 4,338,765 A | 7/1982 | Ohmori et al. |
| 4,377,106 A | 3/1983 | Workman et al. |
| 4,434,908 A | 3/1984 | French |
| 4,456,016 A | 6/1984 | Nowacki et al. |
| 4,463,867 A | 8/1984 | Nagel |
| 4,467,965 A | 8/1984 | Skinner |
| 4,474,302 A | 10/1984 | Goldberg et al. |
| 4,476,116 A | 10/1984 | Anik |
| 4,515,586 A | 5/1985 | Mendenhall et al. |
| 4,516,967 A | 5/1985 | Kopfer |
| 4,524,888 A | 6/1985 | Tada |
| 4,603,794 A | 8/1986 | DeFord et al. |
| 4,677,975 A | 7/1987 | Edgar et al. |
| 4,727,985 A | 3/1988 | McNeirney et al. |
| 4,749,082 A | 6/1988 | Gardiner et al. |
| 4,796,614 A | 1/1989 | Nowacki et al. |
| 4,805,377 A | 2/1989 | Carter |
| 4,813,210 A | 3/1989 | Masuda et al. |
| 4,821,923 A | 4/1989 | Skorka |
| 4,840,017 A | 6/1989 | Miller et al. |
| 4,863,720 A | 9/1989 | Burghart et al. |
| 4,868,582 A | 9/1989 | Dreinhoff |
| 4,885,164 A | 12/1989 | Thurow |
| 4,905,450 A | 3/1990 | Hansen et al. |
| 4,926,613 A | 5/1990 | Hansen |
| 4,951,661 A | 8/1990 | Sladek |
| 4,952,310 A | 8/1990 | McMahan et al. |
| 4,964,540 A | 10/1990 | Katz |
| RE33,444 E | 11/1990 | Lemer |
| 4,973,318 A | 11/1990 | Holm et al. |
| 4,979,941 A | 12/1990 | Ogle, II |
| 4,982,875 A | 1/1991 | Pozzi et al. |
| 5,014,492 A | 5/1991 | Fiorini et al. |
| 5,025,957 A | 6/1991 | Ranalletta et al. |
| 5,059,187 A | 10/1991 | Sperry et al. |
| 5,060,791 A | 10/1991 | Zulauf |
| 5,067,655 A | 11/1991 | Farago et al. |
| 5,156,918 A | 10/1992 | Marks et al. |
| 5,174,366 A | 12/1992 | Nagakura et al. |
| 5,207,217 A | 5/1993 | Cocozza et al. |
| 5,230,884 A | 7/1993 | Evans et al. |
| 5,237,797 A | 8/1993 | Varlet |
| 5,246,142 A | 9/1993 | DiPalma et al. |
| 5,261,565 A | 11/1993 | Drobish et al. |
| 5,263,842 A | 11/1993 | Fealey |
| 5,271,153 A | 12/1993 | Reiboldt et al. |
| 5,282,304 A | 2/1994 | Reiboldt et al. |
| 5,282,549 A | 2/1994 | Scholz et al. |
| 5,284,133 A | 2/1994 | Burns et al. |
| 5,289,948 A | 3/1994 | Moss et al. |
| 5,339,990 A | 8/1994 | Wilder |
| 5,352,196 A | 10/1994 | Haber et al. |
| 5,380,281 A | 1/1995 | Tomellini et al. |
| 5,385,140 A | 1/1995 | Smith |
| 5,394,866 A | 3/1995 | Ritson et al. |
| 5,408,994 A | 4/1995 | Wass et al. |
| 5,433,343 A | 7/1995 | Meshberg |
| 5,435,282 A | 7/1995 | Haber et al. |
| 5,435,884 A | 7/1995 | Simmons et al. |
| 5,451,569 A | 9/1995 | Wong et al. |
| 5,456,522 A | 10/1995 | Beach |
| 5,456,533 A | 10/1995 | Streiff et al. |
| 5,472,143 A | 12/1995 | Bartels et al. |
| 5,482,030 A | 1/1996 | Klein |
| 5,487,378 A | 1/1996 | Robertson et al. |
| 5,497,944 A | 3/1996 | Weston et al. |
| 5,499,750 A | 3/1996 | Manifold |
| 5,499,751 A | 3/1996 | Meyer |
| 5,503,869 A | 4/1996 | Van Oort |
| 5,509,404 A | 4/1996 | Lloyd et al. |
| 5,518,147 A | 5/1996 | Peterson et al. |
| 5,533,994 A | 7/1996 | Meyer |
| 5,541,569 A | 7/1996 | Jang |
| 5,544,646 A | 8/1996 | Lloyd et al. |
| 5,547,094 A | 8/1996 | Bartels et al. |
| 5,569,191 A | 10/1996 | Meyer |
| 5,574,006 A | 11/1996 | Yanagawa |
| 5,579,760 A | 12/1996 | Kohler |
| 5,584,285 A | 12/1996 | Salter et al. |
| 5,593,069 A | 1/1997 | Jinks |
| 5,599,297 A | 2/1997 | Chin et al. |

(56) References Cited

U.S. PATENT DOCUMENTS

| | | |
|---|---|---|
| 5,603,943 A | 2/1997 | Yanagawa |
| 5,614,172 A | 3/1997 | Geimer |
| 5,622,162 A | 4/1997 | Johansson et al. |
| 5,622,163 A | 4/1997 | Jewett et al. |
| 5,643,868 A | 7/1997 | Weiner et al. |
| 5,662,098 A | 9/1997 | Yoshida |
| 5,662,271 A | 9/1997 | Weston et al. |
| 5,676,930 A | 10/1997 | Jager et al. |
| 5,685,846 A | 11/1997 | Michaels, Jr. |
| 5,697,242 A | 12/1997 | Halasz et al. |
| 5,709,202 A | 1/1998 | Lloyd et al. |
| 5,722,598 A | 3/1998 | Werding |
| 5,738,087 A | 4/1998 | King |
| 5,740,967 A | 4/1998 | Simmons et al. |
| 5,763,396 A | 6/1998 | Weiner et al. |
| 5,775,321 A | 7/1998 | Alband |
| 5,782,345 A | 7/1998 | Guasch et al. |
| 5,827,262 A | 10/1998 | Neftel et al. |
| 5,829,435 A | 11/1998 | Rubsamen et al. |
| 5,833,088 A | 11/1998 | Kladders et al. |
| 5,848,588 A | 12/1998 | Foley et al. |
| 5,868,287 A | 2/1999 | Kurokawa et al. |
| 5,881,718 A | 3/1999 | Mortensen et al. |
| 5,884,620 A | 3/1999 | Gonda et al. |
| 5,902,298 A | 5/1999 | Niedospial, Jr. et al. |
| 5,934,272 A | 8/1999 | Lloyd et al. |
| 5,935,101 A | 8/1999 | Kato et al. |
| 5,941,244 A | 8/1999 | Yamazaki et al. |
| 5,950,016 A | 9/1999 | Tanaka |
| 5,950,403 A | 9/1999 | Yamaguchi et al. |
| 5,951,882 A | 9/1999 | Simmons et al. |
| 5,964,416 A | 10/1999 | Jaeger et al. |
| 5,975,370 A | 11/1999 | Durliat |
| 5,997,263 A | 12/1999 | Van Lintel et al. |
| 6,041,777 A | 3/2000 | Faithfull et al. |
| 6,041,969 A | 3/2000 | Parise |
| 6,053,368 A | 4/2000 | Geimer |
| 6,062,430 A | 5/2000 | Fuchs |
| 6,098,618 A | 8/2000 | Jennings et al. |
| 6,109,479 A | 8/2000 | Ruckdeschel |
| 6,110,247 A | 8/2000 | Birmingham et al. |
| 6,116,233 A | 9/2000 | Denyer et al. |
| 6,119,853 A | 9/2000 | Garrill et al. |
| 6,120,492 A | 9/2000 | Finch et al. |
| 6,123,068 A | 9/2000 | Lloyd et al. |
| 6,131,566 A | 10/2000 | Ashurst et al. |
| 6,145,703 A | 11/2000 | Opperman |
| 6,149,054 A | 11/2000 | Cirrillo et al. |
| 6,152,296 A | 11/2000 | Shih |
| 6,171,972 B1 | 1/2001 | Mehregany et al. |
| 6,176,442 B1 | 1/2001 | Eicher et al. |
| 6,179,118 B1 | 1/2001 | Garrill et al. |
| 6,186,409 B1 | 2/2001 | Srinath et al. |
| 6,199,766 B1 | 3/2001 | Fox et al. |
| 6,223,933 B1 | 5/2001 | Hochrainer et al. |
| 6,224,568 B1 | 5/2001 | Morimoto et al. |
| 6,237,589 B1 | 5/2001 | Denyer et al. |
| 6,259,654 B1 | 7/2001 | de la Huerga |
| 6,267,154 B1 | 7/2001 | Felicelli et al. |
| 6,279,786 B1 | 8/2001 | de Pous et al. |
| 6,302,101 B1 | 10/2001 | Py |
| 6,315,173 B1 | 11/2001 | Di Giovanni et al. |
| 6,319,943 B1 | 11/2001 | Joshi et al. |
| 6,336,453 B1 | 1/2002 | Scarrott et al. |
| 6,341,718 B1 | 1/2002 | Schilthuizen et al. |
| 6,349,856 B1 | 2/2002 | Chastel |
| 6,352,152 B1 | 3/2002 | Anderson et al. |
| 6,352,181 B1 | 3/2002 | Eberhard et al. |
| 6,363,932 B1 | 4/2002 | Forchione et al. |
| 6,375,048 B1 | 4/2002 | Van Der Meer et al. |
| 6,392,962 B1 | 5/2002 | Wyatt |
| 6,395,331 B1 | 5/2002 | Yan et al. |
| 6,401,710 B1 | 6/2002 | Scheuch et al. |
| 6,401,987 B1 | 6/2002 | Dechsel et al. |
| 6,402,055 B1 | 6/2002 | Jaeger et al. |
| 6,405,872 B1 | 6/2002 | Ruther et al. |
| 6,412,659 B1 | 7/2002 | Kneer |
| 6,419,167 B1 | 7/2002 | Fuchs |
| 6,423,298 B2 | 7/2002 | McNamara et al. |
| 6,427,682 B1 | 8/2002 | Klimowicz et al. |
| 6,446,054 B1 | 9/2002 | Mayorga Lopez |
| 6,457,658 B2 | 10/2002 | Srinath et al. |
| 6,464,108 B2 | 10/2002 | Corba |
| 6,481,435 B2 | 11/2002 | Hochrainer et al. |
| 6,491,897 B1 | 12/2002 | Freund et al. |
| 6,503,362 B1 | 1/2003 | Bartels et al. |
| 6,513,519 B2 | 2/2003 | Gallem |
| 6,543,448 B1 | 4/2003 | Smith et al. |
| 6,548,647 B2 | 4/2003 | Dietz et al. |
| 6,550,477 B1 | 4/2003 | Casper et al. |
| 6,565,743 B1 | 5/2003 | Poirier et al. |
| 6,578,741 B2 | 6/2003 | Ritsche et al. |
| 6,581,596 B1 | 6/2003 | Truitt et al. |
| 6,584,976 B2 | 7/2003 | Japuntich et al. |
| 6,606,990 B2 | 8/2003 | Stapleton et al. |
| 6,620,438 B2 | 9/2003 | Pairet et al. |
| 6,626,309 B1 | 9/2003 | Jansen et al. |
| 6,640,805 B2 | 11/2003 | Castro et al. |
| 6,641,782 B1 | 11/2003 | Mauchan et al. |
| 6,669,176 B2 | 12/2003 | Rock |
| 6,679,254 B1 | 1/2004 | Rand et al. |
| 6,685,691 B1 | 2/2004 | Freund et al. |
| 6,698,421 B2 | 3/2004 | Attolini |
| 6,706,726 B2 | 3/2004 | Meissner et al. |
| 6,708,846 B1 | 3/2004 | Fuchs et al. |
| 6,725,858 B2 | 4/2004 | Loescher |
| 6,729,328 B2 | 5/2004 | Goldemann |
| 6,732,731 B1 | 5/2004 | Tseng |
| 6,745,763 B2 | 6/2004 | Webb |
| 6,779,520 B2 | 8/2004 | Genova et al. |
| 6,789,702 B2 | 9/2004 | O'Connor et al. |
| 6,792,945 B2 | 9/2004 | Davies et al. |
| 6,823,862 B2 | 11/2004 | McNaughton |
| 6,825,441 B2 | 11/2004 | Katooka et al. |
| 6,846,413 B1 | 1/2005 | Kadel et al. |
| 6,866,039 B1 | 3/2005 | Wright et al. |
| 6,889,690 B2 | 5/2005 | Crowder et al. |
| 6,890,517 B2 | 5/2005 | Drechsel et al. |
| 6,915,901 B2 | 7/2005 | Feinberg et al. |
| 6,929,004 B1 | 8/2005 | Bonney et al. |
| 6,932,962 B1 | 8/2005 | Backstrom et al. |
| 6,942,127 B2 | 9/2005 | Raats |
| 6,964,759 B2 | 11/2005 | Lewis et al. |
| 6,977,042 B2 | 12/2005 | Kadel et al. |
| 6,978,916 B2 | 12/2005 | Smith |
| 6,986,346 B2 | 1/2006 | Hochrainer et al. |
| 6,988,496 B1 | 1/2006 | Eicher et al. |
| 6,994,083 B2 | 2/2006 | Foley et al. |
| 7,040,311 B2 | 5/2006 | Hochrainer et al. |
| 7,066,408 B2 | 6/2006 | Sugimoto et al. |
| 7,090,093 B2 | 8/2006 | Hochrainer et al. |
| 7,131,441 B1 | 11/2006 | Keller et al. |
| 7,152,760 B1 | 12/2006 | Peabody |
| 7,258,716 B2 | 8/2007 | Shekarriz et al. |
| 7,314,187 B2 | 1/2008 | Hochrainer et al. |
| 7,331,340 B2 | 2/2008 | Barney |
| 7,341,208 B2 | 3/2008 | Peters et al. |
| 7,380,575 B2 | 6/2008 | Stricklin |
| 7,417,051 B2 | 8/2008 | Banholzer et al. |
| 7,451,876 B2 | 11/2008 | Bossi et al. |
| 7,470,422 B2 | 12/2008 | Freund et al. |
| 7,556,037 B2 | 7/2009 | Klein |
| 7,559,597 B2 | 7/2009 | Mori |
| 7,571,722 B2 | 8/2009 | Wuttke et al. |
| 7,579,358 B2 | 8/2009 | Boeck et al. |
| 7,611,694 B2 | 11/2009 | Schmidt |
| 7,611,709 B2 | 11/2009 | Bassarab et al. |
| 7,621,266 B2 | 11/2009 | Kladders et al. |
| 7,645,383 B2 | 1/2010 | Kadel et al. |
| 7,652,030 B2 | 1/2010 | Moesgaard et al. |
| 7,665,461 B2 | 2/2010 | Zierenberg et al. |
| 7,681,811 B2 | 3/2010 | Geser et al. |
| 7,686,014 B2 | 3/2010 | Boehm et al. |
| 7,717,299 B2 | 5/2010 | Greiner-Perth |

(56) References Cited

U.S. PATENT DOCUMENTS

| | | |
|---|---|---|
| 7,723,306 B2 | 5/2010 | Bassarab et al. |
| 7,743,945 B2 | 6/2010 | Lu et al. |
| 7,779,838 B2 | 8/2010 | Hetzer et al. |
| 7,802,568 B2 | 9/2010 | Eicher et al. |
| 7,819,342 B2 | 10/2010 | Spallek et al. |
| 7,823,584 B2 | 11/2010 | Geser et al. |
| 7,837,235 B2 | 11/2010 | Geser et al. |
| 7,849,851 B2 | 12/2010 | Zierenberg et al. |
| 7,896,264 B2 | 3/2011 | Eicher et al. |
| 7,980,243 B2 | 7/2011 | Hochrainer |
| 7,994,188 B2 | 8/2011 | Disse |
| 8,062,626 B2 | 11/2011 | Freund et al. |
| 8,104,643 B2 | 1/2012 | Pruvot |
| 8,167,171 B2 | 5/2012 | Moretti |
| 8,298,622 B2 | 10/2012 | Nakayama et al. |
| 8,479,725 B2 | 7/2013 | Hausmann et al. |
| 8,495,901 B2 | 7/2013 | Hahn et al. |
| 8,650,840 B2 | 2/2014 | Holakovsky et al. |
| 8,651,338 B2 | 2/2014 | Leak et al. |
| 8,656,910 B2 | 2/2014 | Boeck |
| 8,733,341 B2 | 5/2014 | Boeck et al. |
| 8,734,392 B2 | 5/2014 | Stadelhofer |
| 8,944,292 B2 | 2/2015 | Moreau |
| 8,950,393 B2 | 2/2015 | Holakovsky et al. |
| 8,960,188 B2 | 2/2015 | Bach et al. |
| 8,997,735 B2 | 4/2015 | Zierenberg et al. |
| 9,027,854 B2 | 5/2015 | Moser et al. |
| 9,192,734 B2 | 11/2015 | Hausmann et al. |
| 9,238,031 B2 | 1/2016 | Schmelzer et al. |
| 9,744,313 B2 | 8/2017 | Besseler et al. |
| 2001/0008632 A1 | 7/2001 | Freund et al. |
| 2001/0028308 A1 | 10/2001 | De La Huerga |
| 2001/0032643 A1 | 10/2001 | Hochrainer et al. |
| 2001/0035182 A1 | 11/2001 | Rubin et al. |
| 2002/0000225 A1 | 1/2002 | Schuler et al. |
| 2002/0005195 A1 | 1/2002 | Shick et al. |
| 2002/0007155 A1 | 1/2002 | Freund et al. |
| 2002/0046751 A1 | 4/2002 | MacRae et al. |
| 2002/0060255 A1 | 5/2002 | Benoist |
| 2002/0074429 A1 | 6/2002 | Hettrich et al. |
| 2002/0079285 A1 | 6/2002 | Jansen et al. |
| 2002/0092523 A1 | 7/2002 | Connelly et al. |
| 2002/0111363 A1 | 8/2002 | Drechsel et al. |
| 2002/0129812 A1 | 9/2002 | Litherland et al. |
| 2002/0130195 A1 | 9/2002 | Jaeger et al. |
| 2002/0137764 A1 | 9/2002 | Drechsel et al. |
| 2002/0176788 A1 | 11/2002 | Moutafis et al. |
| 2003/0039915 A1 | 2/2003 | Holt et al. |
| 2003/0064032 A1 | 4/2003 | Lamche et al. |
| 2003/0066524 A1 | 4/2003 | Hochrainer et al. |
| 2003/0066815 A1 | 4/2003 | Lucas |
| 2003/0080210 A1 | 5/2003 | Jaeger et al. |
| 2003/0085254 A1 | 5/2003 | Katooka et al. |
| 2003/0098023 A1 | 5/2003 | Drachmann et al. |
| 2003/0106827 A1 | 6/2003 | Cheu et al. |
| 2003/0145849 A1 | 8/2003 | Drinan et al. |
| 2003/0178020 A1 | 9/2003 | Scarrott |
| 2003/0181478 A1 | 9/2003 | Drechsel et al. |
| 2003/0183225 A1 | 10/2003 | Knudsen |
| 2003/0187387 A1 | 10/2003 | Wirt et al. |
| 2003/0191151 A1 | 10/2003 | Chaudry et al. |
| 2003/0194379 A1 | 10/2003 | Brugger et al. |
| 2003/0196660 A1 | 10/2003 | Haveri |
| 2003/0209238 A1 | 11/2003 | Peters et al. |
| 2003/0226907 A1 | 12/2003 | Geser et al. |
| 2004/0004138 A1 | 1/2004 | Hettrich et al. |
| 2004/0010239 A1 | 1/2004 | Hochrainer et al. |
| 2004/0015126 A1 | 1/2004 | Zierenberg et al. |
| 2004/0019073 A1 | 1/2004 | Drechsel et al. |
| 2004/0055907 A1 | 3/2004 | Marco |
| 2004/0060476 A1 | 4/2004 | Sirejacob |
| 2004/0069799 A1 | 4/2004 | Gee et al. |
| 2004/0092428 A1 | 5/2004 | Chen et al. |
| 2004/0094147 A1 | 5/2004 | Schyra et al. |
| 2004/0134494 A1 | 7/2004 | Papania et al. |
| 2004/0134824 A1 | 7/2004 | Chan et al. |
| 2004/0139700 A1 | 7/2004 | Powell et al. |
| 2004/0143235 A1 | 7/2004 | Freund et al. |
| 2004/0164186 A1 | 8/2004 | Kladders et al. |
| 2004/0166065 A1 | 8/2004 | Schmidt |
| 2004/0182867 A1 | 9/2004 | Hochrainer et al. |
| 2004/0184994 A1 | 9/2004 | DeStefano et al. |
| 2004/0194524 A1 | 10/2004 | Jentzsch |
| 2004/0210199 A1 | 10/2004 | Atterbury et al. |
| 2004/0231667 A1 | 11/2004 | Horton et al. |
| 2005/0028812 A1 | 2/2005 | Djupesland |
| 2005/0028815 A1 | 2/2005 | Deaton et al. |
| 2005/0028816 A1 | 2/2005 | Fishman et al. |
| 2005/0061314 A1 | 3/2005 | Davies et al. |
| 2005/0089478 A1 | 4/2005 | Govind et al. |
| 2005/0098172 A1 | 5/2005 | Anderson |
| 2005/0126469 A1 | 6/2005 | Lu |
| 2005/0131357 A1 | 6/2005 | Denton et al. |
| 2005/0158394 A1 | 7/2005 | Staniforth et al. |
| 2005/0159441 A1 | 7/2005 | Hochrainer et al. |
| 2005/0183718 A1 | 8/2005 | Wuttke et al. |
| 2005/0191246 A1 | 9/2005 | Bechtold-Peters et al. |
| 2005/0194472 A1 | 9/2005 | Geser et al. |
| 2005/0239778 A1 | 10/2005 | Konetzki et al. |
| 2005/0247305 A1 | 11/2005 | Zierenberg et al. |
| 2005/0250704 A1 | 11/2005 | Bassarab et al. |
| 2005/0250705 A1 | 11/2005 | Bassarab et al. |
| 2005/0255119 A1 | 11/2005 | Bassarab et al. |
| 2005/0263618 A1 | 12/2005 | Spallek et al. |
| 2005/0268909 A1 | 12/2005 | Bonney et al. |
| 2005/0268915 A1 | 12/2005 | Wassenaar et al. |
| 2005/0269359 A1 | 12/2005 | Raats |
| 2006/0002863 A1 | 1/2006 | Schmelzer et al. |
| 2006/0016449 A1 | 1/2006 | Eicher et al. |
| 2006/0035874 A1 | 2/2006 | Lulla et al. |
| 2006/0037612 A1 | 2/2006 | Herder et al. |
| 2006/0067952 A1 | 3/2006 | Chen |
| 2006/0086828 A1 | 4/2006 | Bougamont et al. |
| 2006/0150971 A1 | 7/2006 | Lee et al. |
| 2006/0196500 A1 | 9/2006 | Hochrainer et al. |
| 2006/0225734 A1 | 10/2006 | Sagaser et al. |
| 2006/0239886 A1 | 10/2006 | Nakayama et al. |
| 2006/0239930 A1 | 10/2006 | Lamche et al. |
| 2006/0254579 A1 | 11/2006 | Grychowski et al. |
| 2006/0279588 A1 | 12/2006 | Yearworth et al. |
| 2006/0282045 A1 | 12/2006 | Wilkinson et al. |
| 2006/0285987 A1 | 12/2006 | Jaeger et al. |
| 2006/0289002 A1 | 12/2006 | Hetzer et al. |
| 2006/0293293 A1 | 12/2006 | Muller et al. |
| 2007/0062518 A1 | 3/2007 | Geser et al. |
| 2007/0062519 A1 | 3/2007 | Wuttke et al. |
| 2007/0062979 A1 | 3/2007 | Dunne |
| 2007/0090205 A1 | 4/2007 | Kunze et al. |
| 2007/0090576 A1 | 4/2007 | Geser et al. |
| 2007/0107720 A1 | 5/2007 | Boeck et al. |
| 2007/0119449 A1 | 5/2007 | Boehm et al. |
| 2007/0137643 A1 | 6/2007 | Bonney et al. |
| 2007/0163574 A1 | 7/2007 | Rohrschneider et al. |
| 2007/0181526 A1 | 8/2007 | Frishman |
| 2007/0183982 A1 | 8/2007 | Berkel et al. |
| 2007/0210121 A1 | 9/2007 | Stadelhofer et al. |
| 2007/0221211 A1 | 9/2007 | Sagalovich |
| 2007/0264437 A1 | 11/2007 | Zimmermann et al. |
| 2007/0272763 A1 | 11/2007 | Dunne et al. |
| 2007/0298116 A1 | 12/2007 | Bechtold-Peters et al. |
| 2008/0017192 A1 | 1/2008 | Southby et al. |
| 2008/0029085 A1 | 2/2008 | Lawrence et al. |
| 2008/0060640 A1 | 3/2008 | Waldner et al. |
| 2008/0083408 A1 | 4/2008 | Hodson et al. |
| 2008/0092885 A1 | 4/2008 | von Schuckmann |
| 2008/0156321 A1 | 7/2008 | Bowman et al. |
| 2008/0163869 A1 | 7/2008 | Nobutani et al. |
| 2008/0197045 A1 | 8/2008 | Metzger et al. |
| 2008/0249459 A1 | 10/2008 | Godfrey et al. |
| 2008/0264412 A1 | 10/2008 | Meyer et al. |
| 2008/0265198 A1 | 10/2008 | Warby |
| 2008/0283553 A1 | 11/2008 | Cox et al. |
| 2008/0299049 A1 | 12/2008 | Stangl |
| 2008/0308580 A1 | 12/2008 | Gaydos et al. |

(56) References Cited

U.S. PATENT DOCUMENTS

| | | |
|---|---|---|
| 2009/0032427 A1 | 2/2009 | Cheu et al. |
| 2009/0060764 A1 | 3/2009 | Mitzlaff et al. |
| 2009/0075990 A1 | 3/2009 | Schmidt |
| 2009/0114215 A1 | 5/2009 | Boeck et al. |
| 2009/0166379 A1 | 7/2009 | Wright et al. |
| 2009/0170839 A1 | 7/2009 | Schmidt |
| 2009/0185983 A1 | 7/2009 | Freund et al. |
| 2009/0197841 A1 | 8/2009 | Kreher et al. |
| 2009/0202447 A1 | 8/2009 | Kreher et al. |
| 2009/0211576 A1 | 8/2009 | Lehtonen et al. |
| 2009/0221626 A1 | 9/2009 | Schmidt |
| 2009/0235924 A1 | 9/2009 | Holakovsky et al. |
| 2009/0272664 A1 | 11/2009 | Marshall et al. |
| 2009/0293870 A1 | 12/2009 | Brunnberg et al. |
| 2009/0306065 A1 | 12/2009 | Schmidt |
| 2009/0308772 A1 | 12/2009 | Abrams |
| 2009/0314287 A1 | 12/2009 | Spallek et al. |
| 2009/0317337 A1 | 12/2009 | Schmidt |
| 2010/0012120 A1 | 1/2010 | Herder et al. |
| 2010/0018524 A1 | 1/2010 | Jinks et al. |
| 2010/0018997 A1 | 1/2010 | Faneca Llesera |
| 2010/0044393 A1 | 2/2010 | Moretti |
| 2010/0056559 A1 | 3/2010 | Schmelzer et al. |
| 2010/0084531 A1 | 4/2010 | Schuchman |
| 2010/0095957 A1 | 4/2010 | Corbacho |
| 2010/0144784 A1 | 6/2010 | Schmelzer et al. |
| 2010/0168710 A1 | 7/2010 | Braithwaite |
| 2010/0237102 A1 | 9/2010 | Margheritis |
| 2010/0242557 A1 | 9/2010 | Spreitzer et al. |
| 2010/0242954 A1 | 9/2010 | Hahn et al. |
| 2010/0313884 A1 | 12/2010 | Elliman |
| 2010/0331765 A1 | 12/2010 | Sullivan et al. |
| 2011/0005517 A1 | 1/2011 | Boeck et al. |
| 2011/0041842 A1 | 2/2011 | Bradshaw et al. |
| 2011/0168175 A1 | 7/2011 | Dunne et al. |
| 2011/0239594 A1 | 10/2011 | Nottingham et al. |
| 2011/0245780 A1 | 10/2011 | Helmer et al. |
| 2011/0268668 A1 | 11/2011 | Lamche et al. |
| 2011/0277753 A1 | 11/2011 | Dunne et al. |
| 2011/0290239 A1 | 12/2011 | Bach et al. |
| 2011/0290242 A1 | 12/2011 | Bach et al. |
| 2011/0290243 A1 | 12/2011 | Bach et al. |
| 2012/0090603 A1 | 4/2012 | Dunne et al. |
| 2012/0132199 A1 | 5/2012 | Kiesewetter |
| 2012/0138049 A1 | 6/2012 | Wachtel |
| 2012/0138713 A1 | 6/2012 | Schuy et al. |
| 2012/0260913 A1 | 10/2012 | Bach et al. |
| 2012/0325204 A1 | 12/2012 | Holakovsky et al. |
| 2013/0012908 A1 | 1/2013 | Yeung |
| 2013/0056888 A1 | 3/2013 | Holakovsky et al. |
| 2013/0125880 A1 | 5/2013 | Holakovsky et al. |
| 2013/0125881 A1 | 5/2013 | Holakovsky et al. |
| 2013/0126389 A1 | 5/2013 | Holakovsky et al. |
| 2013/0206136 A1 | 8/2013 | Herrmann et al. |
| 2013/0269687 A1 | 10/2013 | Besseler et al. |
| 2014/0121234 A1 | 5/2014 | Kreher et al. |
| 2014/0190472 A1 | 7/2014 | Holakovsky et al. |
| 2014/0228397 A1 | 8/2014 | Schmelzer et al. |
| 2014/0331994 A1 | 11/2014 | Holakovsky et al. |
| 2015/0040890 A1 | 2/2015 | Besseler et al. |
| 2015/0040893 A1 | 2/2015 | Besseler et al. |
| 2015/0041558 A1 | 2/2015 | Besseler et al. |
| 2015/0122247 A1 | 5/2015 | Besseler et al. |
| 2015/0258021 A1 | 9/2015 | Kreher et al. |
| 2015/0306087 A1 | 10/2015 | Schmelzer et al. |
| 2015/0320947 A1 | 11/2015 | Eicher et al. |
| 2015/0320948 A1 | 11/2015 | Eicher et al. |
| 2016/0095992 A1 | 4/2016 | Wachtel |

FOREIGN PATENT DOCUMENTS

| | | |
|---|---|---|
| CA | 2233981 A1 | 4/1997 |
| CA | 2237853 A1 | 6/1997 |
| CA | 2251828 A1 | 10/1997 |
| CA | 2275392 A1 | 7/1998 |
| CA | 2297174 A1 | 2/1999 |
| CA | 2343123 A1 | 4/2000 |
| CA | 2434872 A1 | 8/2002 |
| CA | 2497059 A1 | 3/2004 |
| CA | 2497680 A1 | 3/2004 |
| CA | 2513167 A1 | 10/2004 |
| CA | 2557020 A1 | 9/2005 |
| CA | 2653183 A1 | 12/2007 |
| CA | 2653422 A1 | 12/2007 |
| CN | 1125426 A | 6/1996 |
| CN | 1849174 A | 10/2006 |
| CN | 101247897 A | 8/2008 |
| DE | 1653651 A1 | 7/1971 |
| DE | 2754100 A1 | 6/1978 |
| DE | 4117078 A1 | 11/1992 |
| DE | 19625027 A1 | 1/1997 |
| DE | 19615422 A1 | 11/1997 |
| DE | 19653969 A1 | 6/1998 |
| DE | 19902844 C1 | 11/1999 |
| DE | 10007591 A1 | 11/2000 |
| DE | 10104367 A1 | 8/2002 |
| DE | 10300983 A1 | 7/2004 |
| DE | 102004031673 A1 | 1/2006 |
| DE | 202006017793 U1 | 1/2007 |
| DE | 01102006025871 A1 | 12/2007 |
| DK | 83175 C | 7/1957 |
| DK | 140801 B | 11/1979 |
| EP | 0018609 A1 | 11/1980 |
| EP | 0289332 A1 | 11/1988 |
| EP | 0289336 A2 | 11/1988 |
| EP | 0354507 A2 | 2/1990 |
| EP | 0364235 A1 | 4/1990 |
| EP | 0372777 A2 | 6/1990 |
| EP | 0386800 A1 | 9/1990 |
| EP | 0412524 A1 | 2/1991 |
| EP | 0505123 A1 | 9/1992 |
| EP | 0520571 A1 | 12/1992 |
| EP | 0622311 A2 | 11/1994 |
| EP | 0642992 A2 | 3/1995 |
| EP | 0679443 A1 | 11/1995 |
| EP | 0735048 A1 | 10/1996 |
| EP | 0811430 A1 | 3/1997 |
| EP | 0778221 A1 | 6/1997 |
| EP | 0845253 A2 | 6/1998 |
| EP | 0845265 A1 | 6/1998 |
| EP | 0860210 A2 | 8/1998 |
| EP | 0916428 A2 | 5/1999 |
| EP | 0965355 A2 | 12/1999 |
| EP | 0970751 A2 | 1/2000 |
| EP | 1003478 A1 | 5/2000 |
| EP | 1017469 A1 | 7/2000 |
| EP | 1025923 A1 | 8/2000 |
| EP | 1068906 A2 | 1/2001 |
| EP | 1075875 A2 | 2/2001 |
| EP | 1092447 A2 | 4/2001 |
| EP | 1157689 A1 | 11/2001 |
| EP | 1211628 A2 | 6/2002 |
| EP | 1245244 A2 | 10/2002 |
| EP | 1312418 A2 | 5/2003 |
| EP | 1375385 A2 | 1/2004 |
| EP | 1521609 A2 | 4/2005 |
| EP | 1535643 A1 | 6/2005 |
| EP | 1595564 A1 | 11/2005 |
| EP | 1595822 A1 | 11/2005 |
| EP | 1726324 A1 | 11/2006 |
| EP | 1736193 A1 | 12/2006 |
| EP | 1795221 A1 | 6/2007 |
| EP | 1813548 A1 | 8/2007 |
| EP | 2135632 A1 | 12/2009 |
| ES | 2262348 T3 | 11/2006 |
| FR | 2505688 A1 | 11/1982 |
| FR | 2604363 A1 | 4/1988 |
| FR | 2673608 A1 | 9/1992 |
| FR | 2756502 A1 | 6/1998 |
| GB | 1524431 A | 9/1978 |
| GB | 2081396 | 2/1982 |
| GB | 2101020 A | 1/1983 |
| GB | 2279273 A | 1/1995 |
| GB | 2291135 A | 1/1996 |

(56) References Cited

FOREIGN PATENT DOCUMENTS

| | | | |
|---|---|---|---|
| GB | 2332372 A | 6/1999 |
| GB | 2333129 A | 7/1999 |
| GB | 2347870 A | 9/2000 |
| GB | 2355252 A | 4/2001 |
| GB | 2398253 A | 8/2004 |
| GB | 0700839.4 | 7/2008 |
| JP | S5684246 A | 7/1981 |
| JP | H01288265 A | 11/1989 |
| JP | H0228121 A | 1/1990 |
| JP | H057246 | 2/1993 |
| JP | H0553470 A | 3/1993 |
| JP | H06312019 A | 11/1994 |
| JP | H07118164 A | 5/1995 |
| JP | H07118166 A | 5/1995 |
| JP | 07323086 A | 12/1995 |
| JP | H08277226 A | 10/1996 |
| JP | H092442 A | 1/1997 |
| JP | H0977073 A | 3/1997 |
| JP | H09315953 A | 12/1997 |
| JP | 2001518428 A | 10/2001 |
| JP | 2001346878 A | 12/2001 |
| JP | 2002504411 A | 2/2002 |
| JP | 2002235940 A | 8/2002 |
| JP | 2003511212 A | 3/2003 |
| JP | 2003299717 A | 10/2003 |
| JP | 2004502502 A | 1/2004 |
| JP | 2004097617 A | 4/2004 |
| JP | 2005511210 A | 4/2005 |
| JP | 2005144459 A | 6/2005 |
| JP | 2007517529 A | 7/2007 |
| JP | 2007245144 A | 9/2007 |
| JP | 2007534379 A | 11/2007 |
| JP | 2008119489 A | 5/2008 |
| JP | 2008541808 A | 11/2008 |
| JP | 2010526620 A | 8/2010 |
| JP | 2010540371 A | 12/2010 |
| WO | 198100674 A1 | 3/1981 |
| WO | 198200785 A1 | 3/1982 |
| WO | 198300288 A1 | 2/1983 |
| WO | 198303054 A1 | 9/1983 |
| WO | 198605419 A1 | 9/1986 |
| WO | 198706137 A1 | 10/1987 |
| WO | 198803419 A1 | 5/1988 |
| WO | 198900889 A1 | 2/1989 |
| WO | 198900947 A1 | 2/1989 |
| WO | 198902279 A1 | 3/1989 |
| WO | 198903672 A1 | 5/1989 |
| WO | 198903673 A1 | 5/1989 |
| WO | 198905139 A1 | 6/1989 |
| WO | 199009780 A1 | 9/1990 |
| WO | 199009781 A1 | 9/1990 |
| WO | 1991014468 A1 | 10/1991 |
| WO | 199206704 A1 | 4/1992 |
| WO | 199217231 A1 | 10/1992 |
| WO | 199221332 A1 | 12/1992 |
| WO | 199222286 | 12/1992 |
| WO | 1993013737 A1 | 7/1993 |
| WO | 199325321 A1 | 12/1993 |
| WO | 1993024164 A1 | 12/1993 |
| WO | 1994007607 A1 | 4/1994 |
| WO | 199417822 A1 | 8/1994 |
| WO | 199425371 A1 | 11/1994 |
| WO | 199427653 A2 | 12/1994 |
| WO | 199503034 A1 | 2/1995 |
| WO | 1995032015 A1 | 11/1995 |
| WO | 199600050 A1 | 1/1996 |
| WO | 1996006011 | 2/1996 |
| WO | 199606581 A1 | 3/1996 |
| WO | 199623522 A1 | 8/1996 |
| WO | 199701329 A1 | 1/1997 |
| WO | 199706813 A1 | 2/1997 |
| WO | 199706842 A1 | 2/1997 |
| WO | 199712683 A1 | 4/1997 |
| WO | 1997012687 A1 | 4/1997 |
| WO | 199720590 A1 | 6/1997 |
| WO | 199723208 A1 | 7/1997 |
| WO | 199727804 A1 | 8/1997 |
| WO | 199735562 A1 | 10/1997 |
| WO | 199741833 A1 | 11/1997 |
| WO | 1998012511 A2 | 3/1998 |
| WO | 199827959 A2 | 7/1998 |
| WO | 199831346 A1 | 7/1998 |
| WO | 199839043 A1 | 9/1998 |
| WO | 1999001227 A1 | 1/1999 |
| WO | 1999007340 A1 | 2/1999 |
| WO | 1999011563 A1 | 3/1999 |
| WO | 1999016530 A1 | 4/1999 |
| WO | 1999043571 A1 | 9/1999 |
| WO | 199962495 A2 | 12/1999 |
| WO | 199965464 | 12/1999 |
| WO | 200001612 A2 | 1/2000 |
| WO | 200023037 A1 | 4/2000 |
| WO | 2000023065 A2 | 4/2000 |
| WO | 200027543 A1 | 5/2000 |
| WO | 200037336 A1 | 6/2000 |
| WO | 2000033965 A1 | 6/2000 |
| WO | 200049988 A2 | 8/2000 |
| WO | 200064779 A1 | 11/2000 |
| WO | 200113885 A1 | 3/2001 |
| WO | 200128489 A1 | 4/2001 |
| WO | 2001064182 A2 | 9/2001 |
| WO | 200187392 A2 | 11/2001 |
| WO | 2001085097 A2 | 11/2001 |
| WO | 200197888 A2 | 12/2001 |
| WO | 200198175 A1 | 12/2001 |
| WO | 200198176 A2 | 12/2001 |
| WO | 200204054 A1 | 1/2002 |
| WO | 200205879 A1 | 1/2002 |
| WO | 200217988 A2 | 3/2002 |
| WO | 200232899 A1 | 4/2002 |
| WO | 2002034411 A1 | 5/2002 |
| WO | 2002070141 A1 | 9/2002 |
| WO | 2002089887 A1 | 11/2002 |
| WO | 2003002045 A1 | 1/2003 |
| WO | 2003014832 A1 | 2/2003 |
| WO | 2003020253 A2 | 3/2003 |
| WO | 2003022332 A2 | 3/2003 |
| WO | 2003035030 A1 | 5/2003 |
| WO | 2003037159 A2 | 5/2003 |
| WO | 2003037259 A2 | 5/2003 |
| WO | 2003049786 A2 | 6/2003 |
| WO | 2003050031 A1 | 6/2003 |
| WO | 2003053350 A2 | 7/2003 |
| WO | 2003057593 A1 | 7/2003 |
| WO | 2003059547 A1 | 7/2003 |
| WO | 2003068299 A1 | 8/2003 |
| WO | 2003087097 A1 | 10/2003 |
| WO | 2003097139 A1 | 11/2003 |
| WO | 2004019985 A1 | 3/2004 |
| WO | 2004022052 A1 | 3/2004 |
| WO | 2004022132 A2 | 3/2004 |
| WO | 2004022244 A1 | 3/2004 |
| WO | 2004024157 A1 | 3/2004 |
| WO | 200433954 A2 | 4/2004 |
| WO | 2004062813 A1 | 7/2004 |
| WO | 2004078236 A2 | 9/2004 |
| WO | 2004089551 A2 | 10/2004 |
| WO | 2004091704 A1 | 10/2004 |
| WO | 2004098689 A1 | 11/2004 |
| WO | 2004098795 A1 | 11/2004 |
| WO | 2005000476 A1 | 1/2005 |
| WO | 2005004844 A1 | 1/2005 |
| WO | 2005014175 A1 | 2/2005 |
| WO | 2005020953 A1 | 3/2005 |
| WO | 2005030211 A1 | 4/2005 |
| WO | 2005055976 A2 | 6/2005 |
| WO | 2005077445 A1 | 8/2005 |
| WO | 2005079997 A1 | 9/2005 |
| WO | 2005080001 A1 | 9/2005 |
| WO | 2005080002 A1 | 9/2005 |
| WO | 2005087299 A1 | 9/2005 |
| WO | 2005107837 A1 | 11/2005 |
| WO | 2005109948 A2 | 11/2005 |
| WO | 2005112892 A1 | 12/2005 |

(56) References Cited

FOREIGN PATENT DOCUMENTS

| | | |
|---|---|---|
| WO | 2005112996 A1 | 12/2005 |
| WO | 2005113007 A2 | 12/2005 |
| WO | 2006011638 A1 | 2/2006 |
| WO | 2006018392 A1 | 2/2006 |
| WO | 2006027595 A1 | 3/2006 |
| WO | 2006037636 A2 | 4/2006 |
| WO | 2006037948 A2 | 4/2006 |
| WO | 2006042297 A2 | 4/2006 |
| WO | 2006045813 A1 | 5/2006 |
| WO | 2006110080 A1 | 10/2006 |
| WO | 2006125577 A2 | 11/2006 |
| WO | 2006126014 A2 | 11/2006 |
| WO | 2007011475 A1 | 1/2007 |
| WO | 2007022898 A2 | 3/2007 |
| WO | 2007030162 A2 | 3/2007 |
| WO | 20070022898 A2 | 3/2007 |
| WO | 2007049239 A2 | 5/2007 |
| WO | 2007060104 A2 | 5/2007 |
| WO | 2007060105 A1 | 5/2007 |
| WO | 2007060106 A1 | 5/2007 |
| WO | 2007060107 A1 | 5/2007 |
| WO | 2007060108 A2 | 5/2007 |
| WO | 2007062721 A1 | 6/2007 |
| WO | 2007090822 A2 | 8/2007 |
| WO | 2007101557 A2 | 9/2007 |
| WO | 2007128381 A1 | 11/2007 |
| WO | 2007134965 A1 | 11/2007 |
| WO | 2007134966 A1 | 11/2007 |
| WO | 2007134967 A1 | 11/2007 |
| WO | 2007134968 A1 | 11/2007 |
| WO | 2007141201 A1 | 12/2007 |
| WO | 2007141203 A1 | 12/2007 |
| WO | 2008023017 A2 | 2/2008 |
| WO | 2008047035 A2 | 4/2008 |
| WO | 2008077623 A1 | 7/2008 |
| WO | 2008124666 A2 | 10/2008 |
| WO | 2008138936 A2 | 11/2008 |
| WO | 2008146025 A2 | 12/2008 |
| WO | 2009006137 A1 | 1/2009 |
| WO | 2009047021 A1 | 4/2009 |
| WO | 2009047173 A2 | 4/2009 |
| WO | 2009050978 A1 | 4/2009 |
| WO | 20090047173 A2 | 4/2009 |
| WO | 2009090245 A1 | 7/2009 |
| WO | 2009103510 A1 | 8/2009 |
| WO | 2009115200 A1 | 9/2009 |
| WO | 2010005946 A2 | 1/2010 |
| WO | 2010006870 A1 | 1/2010 |
| WO | 2010094305 A1 | 8/2010 |
| WO | 2010094413 A2 | 8/2010 |
| WO | 2010112358 A2 | 10/2010 |
| WO | 2010133294 A2 | 11/2010 |
| WO | 2010149280 A1 | 12/2010 |
| WO | 2011006711 A1 | 1/2011 |
| WO | 2011064160 A1 | 6/2011 |
| WO | 2011064163 A1 | 6/2011 |
| WO | 2011064164 A1 | 6/2011 |
| WO | 2011131779 A1 | 10/2011 |
| WO | 2011154295 A2 | 12/2011 |
| WO | 2011160932 A1 | 12/2011 |
| WO | 2012130757 A1 | 10/2012 |
| WO | 2012159914 A1 | 11/2012 |
| WO | 2012160047 A2 | 11/2012 |
| WO | 2012160052 A1 | 11/2012 |
| WO | 2012161685 A1 | 11/2012 |
| WO | 2012162305 A1 | 11/2012 |
| WO | 2013017640 A1 | 2/2013 |
| WO | 2013110601 A1 | 8/2013 |
| WO | 2013152861 A1 | 10/2013 |
| WO | 2013152894 A1 | 10/2013 |
| WO | 2014111370 A1 | 7/2014 |
| WO | 2015018901 A1 | 2/2015 |
| WO | 2015018903 A1 | 2/2015 |
| WO | 2015018904 A1 | 2/2015 |
| WO | 2015169431 A2 | 11/2015 |
| WO | 2015169732 A1 | 11/2015 |
| ZA | 199901520 A | 12/1999 |

OTHER PUBLICATIONS

Abstract in English for WO2009050978, 2009.
"Lung Cancer". Merck Manual Home Edition, pp. 1-7. [Accessed at www.merck.com/mmhe/print/sec04/ch057/ch057a.html, on Jul. 28, 2010].
Abstract in English for DE19902844, 1999.
Abstract in English for DE4117078, 1992.
Abstract in English for EP0354507, 1990.
Abstract in English for FR2756502, 1998.
Abstract in English for JPS5684246, 1979.
Abstract in English of DE10007591, 2000.
Abstract in English of DE202006017793, 2007.
Abstract in English of FR2604363, Sep. 30, 1986.
Abstract in English of JPH0553470, 1993.
Abstract in English of JPH057246, 1993.
Abstract in English of JPH07118164, 1995.
Abstract in English of JPH07118166, 1995.
Abstract in English of JPH08277226,1996.
Abstract in English of JPH092442, 1997.
Abstract in English of JPH09315953, 1997.
Abstract in English of JPH0977073, 1997.
Abstract in English of WO199706813, 1997.
Abstract in English of WO199839043, 1998.
Abstract in English of WO2002070141, 2002.
Ackermann et al.; Quantitative Online Detection of Low-Concentrated Drugs via a SERS Microfluidic System; ChemPhysChem; 2007; vol. 8; No. 18; pp. 2665-2670.
Beasley R et al: "Preservatives in Nebulizer solutions: Risks without Benefit" Pharmacotherapy, Boston, US, Bd. 18, Nr. 1, Jan. 1998.
Beasley R et al: "Preservatives in Nebulizer solutions: Risks without Benefit" Pharmacotherapy, Boston, US, Bd. 18, Mr. 1, Jan. 1998, pp. 130-139.
Bocci et al., "Pulmonary catabolism of interferons: alveolar absorption of 125l-labeled human interferon alpha is accompanied by partial loss of biological activity". Antiviral Research, vol. 4, 1984, pp. 211-220.
Chen, F-K et al., "A study of forming pressure in the tube-hydroforming process". Journal of Materials Processing Technology, 192-193, 2007, p. 404-409.
China Suppliers, Shanghai Lite Chemical Technology Co., Ltd. Product details on polyvinylpyrrolidones. Obtained online by the USPTO examiner on Apr. 24, 2011.
Cras et al., "Comparison of chemical cleaning methods of glass in preparation for silanization". Biosensors & Bioelectronics, vol. 14, 1999, pp. 683-688.
Diamond et al., "Substance P Fails to Mimic Vagally Mediated Nonadrenergic Bronchodilation". Peptides, vol. 3, 1982, pp. 27-29.
Elwenspoek et al., "Silicon Micromachining", Chapter 3, Mechanical Microsensors, Springer-Verlag Berlin Heidelberg, 2001, 4 pages.
English Language Abstract of EP1068906, 2001.
Fuchs et al., "Neopterin, biochemistry and clinical use as a marker for cellular immune reactions". International Archives of Allergy and Immunology, vol. 101, No. 1, 1993, pp. 1-6, Abstract 1p.
Han et al.; Surface activation of thin silicon oxides by wet cleaning and silanization; Thin Solid Films; 2006; vol. 510; No. 1-2; pp. 175-180.
Henkel et al.; Chip modules for generation and manipulation of fluid segments for micro serial flow processes; Chemical Engineering Journal; 2004; vol. 101; pp. 439-445.
Hoffmann et al., "Mixed self-assembled monolayers (SAMs) consisting of methoxy-tri(ethylene glycol)-terminated and alkyl-terminated dimethylchlorosilanes control the non-specific adsorption of proteins at oxidic surfaces". Journal of Colloid and Interface Science, vol. 295, 2006, pp. 427-435.

(56) References Cited

OTHER PUBLICATIONS

Husseini et al., "Alkyl Monolayers on Silica Surfaces Prepared Using Neat, Heated Dimethylmonochlorosilanes with Low Vapor Pressures". Langmuir, vol. 19, 2003, pp. 5169-5171.

Ip et al., "Stability of Recombinant Consensus Interferon to Air-Jet and Ultrasonic Nebulization". Journal of Pharmaceutical Sciences, vol. 84, No. 10, Oct. 1995, pp. 1210-1214.

Jendle et al., "Intrapulmonary administration of insulin to healthy volunteers". Journal of Internal Medicine, vol. 240, 1996, pp. 93-98.

JP2005144459—English language abstract only.

Kutchoukov et al., "Fabrication of nanofluidic devices using glass-to-glass anodic bonding" Sensors and Actuators A, vol. 114, 2004, pp. 521-527.

Lougheed et al., "Insulin Aggregation in Artificial Delivery Systems". Diabetologia, vol. 19, 1980, pp. 1-9.

Mandal et al., "Cytophobic surface modification of microfluidic arrays for in situ parallel peptide synthesis and cell adhesion assays". Biotechnology Progress, vol. 23, No. 4, 2007, pp. 972-978 (Author Manuscript Available in PMC, Sep. 21, 2009, 19 pages).

Niven et al., "Some Factors Associated with the Ultrasonic Nebulization of Proteins". Pharmaceutical Research, vol. 12, No. 1, 1995, pp. 53-59.

Remington Pharmacy, Editor Alfonso R. Gennaro. 19th ed., Spanish Secondary Edition: Panamericana, Spain, 1995, Sciarra, J.J., "Aerosols", pp. 2560-2582. The English translation is from the 1995 English Primary Edition, Sciarra, J.J., Chapter 95, R97-1185.

Trasch et al., "Performance data of refloquant Glucose in the Evaluation of Reflotron". Clinical Chemistry, vol. 30, 1984, p. 969 (abstract only).

Wall et al., "High levels of exopeptidase activity are present in rat and canine bronchoalveolar lavage fluid". International Journal of Pharmaceutics, vol. 97, Issue 1-3, pp. 171-181, 1993, Abstract pp. 1-2.

Wang et al.; Self-Assembled Silane Monolayers: Fabrication with Nanoscale Uniformity; Langmuir; 2005; vol. 21; No. 5; pp. 1848-1857.

"Activate". Collins English Dictionary, London: Collins, 2000, 2 pages. [Retrieved at http://search.credoreference.com/content/entry/hcengdict/activate/0 on Jun. 12, 2014].

International Search Report and Written Opinion for PCT/EP2010/067901, dated Apr. 14, 2011.

NEBULIZER

The present invention relates to a nebulizer for dispensing a fluid.

One starting point for the present invention is a nebulizer illustrated in WO 2006/125577 A2. The nebulizer comprises, as a reservoir for fluid which is to be atomized or nebulized, an insertable rigid container having an inner bag containing the fluid and a pressure generator with a drive spring for delivering and atomizing the fluid. Preferably, the container is secured against removal. For the purpose, the nebulizer of its housing may be designed such that it cannot be opened after the container has been inserted.

Preferably, the container is pre-installed in nebulizer in the delivery state. In particular, the pre-installed container is held by a transportation lock unmovable within the housing in the delivery state in order to avoid any undesired opening of the container.

Before being used for the first time the nebulizer is completely closed. Thus, the pre-installed container is opened by a delivery tube piercing a sealing and a septum to fluidically connect to the inner bag of the container. Further, the transportation lock is opened so that the container can move inside the nebulizer back and forth.

By rotating the lower housing part of the nebulizer the drive spring can be put under tension and fluid can be sucked into a compression chamber of the pressure generator. Simultaneously, the container is moved into the lower housing part in a stroke movement within the nebulizer and when tensioned for the first time the container may be pierced through its base by a piercing element in the lower housing part to allow venting of the container. After manual operation of a locking element the drive spring is released and the fluid in the pressure chamber is put under pressure by the drive spring and is delivered or atomized through a nozzle into a mouthpiece as an aerosol, without the use of propellant gas.

WO 2007/022898 A2 discloses a similar nebulizer. A container can be inserted into a housing of the nebulizer. The housing is closed by a lower or bottom housing part. The container is moving axially forth and back during conveying of the fluid to be nebulized, during pressure generation and/or during nebulization. A counter can be arranged in the housing part. The counter locks the nebulizer against further use if a predetermined number of operations has been reached or exceeded. Then, the housing part may be replaced together with the counter and the container. The container may be connected inseparably with the housing part. However, WO 2007/022898 A2 does not describe a simple and inexpensive construction for connecting the container with the housing part inseparably and such that the container is moveable back and forth within the housing during conveying of the fluid, pressure generation and/or nebulization.

Object of the present invention is to provide a nebulizer with optimized handling and/or simple assembly or construction, even with pre-installed container.

The above object is achieved by a nebulizer as described herein. Preferred embodiments are also described herein.

The nebulizer comprises a securing means for holding the container in the housing or a housing part thereof inseparably, wherein the container is moveable back and forth within the housing during conveying of fluid, pressure generation and/or nebulization. This allows opening of the nebulizer and simultaneously prevents separation of the container from the housing or housing part of the nebulizer.

According to a first aspect of the present invention, the securing means comprises or consists of a metal and/or stamping part. This allows a simple construction and, in particular, integration of the securing means into current designs.

According to a second aspect of the present invention, the securing means consists of a single unitary part. This allows a very simple and inexpensive construction.

According to a third aspect of the present invention, the securing means does not only connect the container inseparably with the housing or housing part such that the container is moveable back and forth within the housing during conveying of the fluid, pressure generation and/or nebulization, but also forms in a transportation lock which holds the container unmoveably in the housing in a delivery state, in particular with the pre-installed container being still closed. This facilitates assembly and avoids any undesired opening of the container in the delivery state. Further, the multiple functions of the securing means simplify construction.

Additionally or alternatively the securing means may comprise an opening means for opening a venting hole of the container. This additional function simplifies the construction as well.

According to a fourth aspect of the present invention, the nebulizer or housing comprises a cage as securing means for holding the container such that the container is moveable back and forth, but is inseparable from the housing or a housing part thereof, and/or such that the container is unmoveably held in a delivery state of the nebulizer. This allows a simple construction. In particular, the cage is ideal for allowing a limited moveability of the container relative to the housing or housing part and simultaneously connecting the container inseparably with the housing or housing part. This allows a very simple and inexpensive construction.

Preferably the nebulizer has the still closed container provided therein and the nebulizer is constructed so that the container is opened inside the nebulizer before or during the first use of the nebulizer. This basic idea is hereinafter called also "pre-installed container". This makes operation easy as there is no need to open the nebulizer, insert the container and close the nebulizer. Moreover, undesirable soiling or damage to the nebulizer caused by incorrect handling when inserting the container can thus be prevented. Accordingly, there is better operational safety as it is impossible for the container to be wrongly inserted or otherwise misused during insertion.

The different aspects of the present invention mentioned above and described in the following can be realized independently from each other and in any combination.

Figure 2:
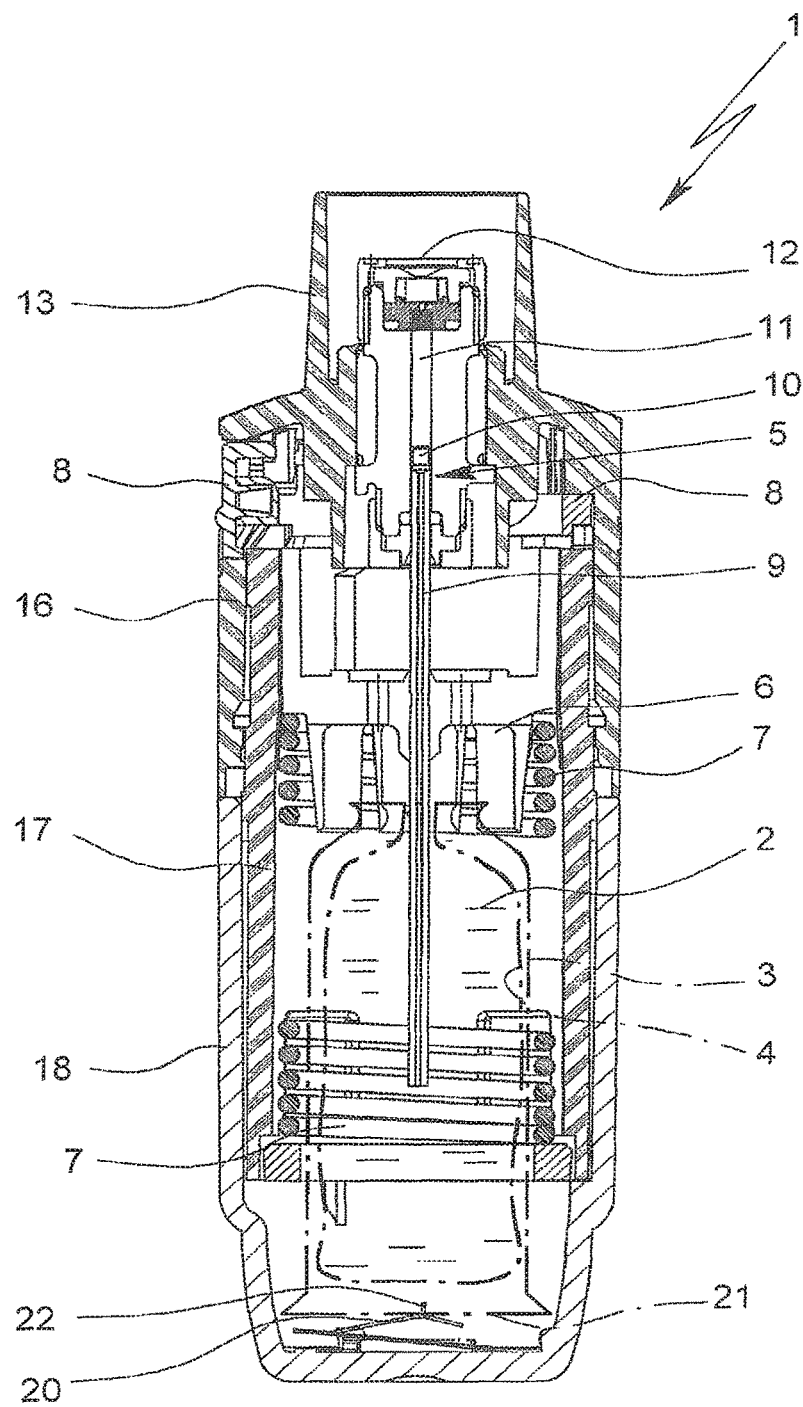
Figure 3:
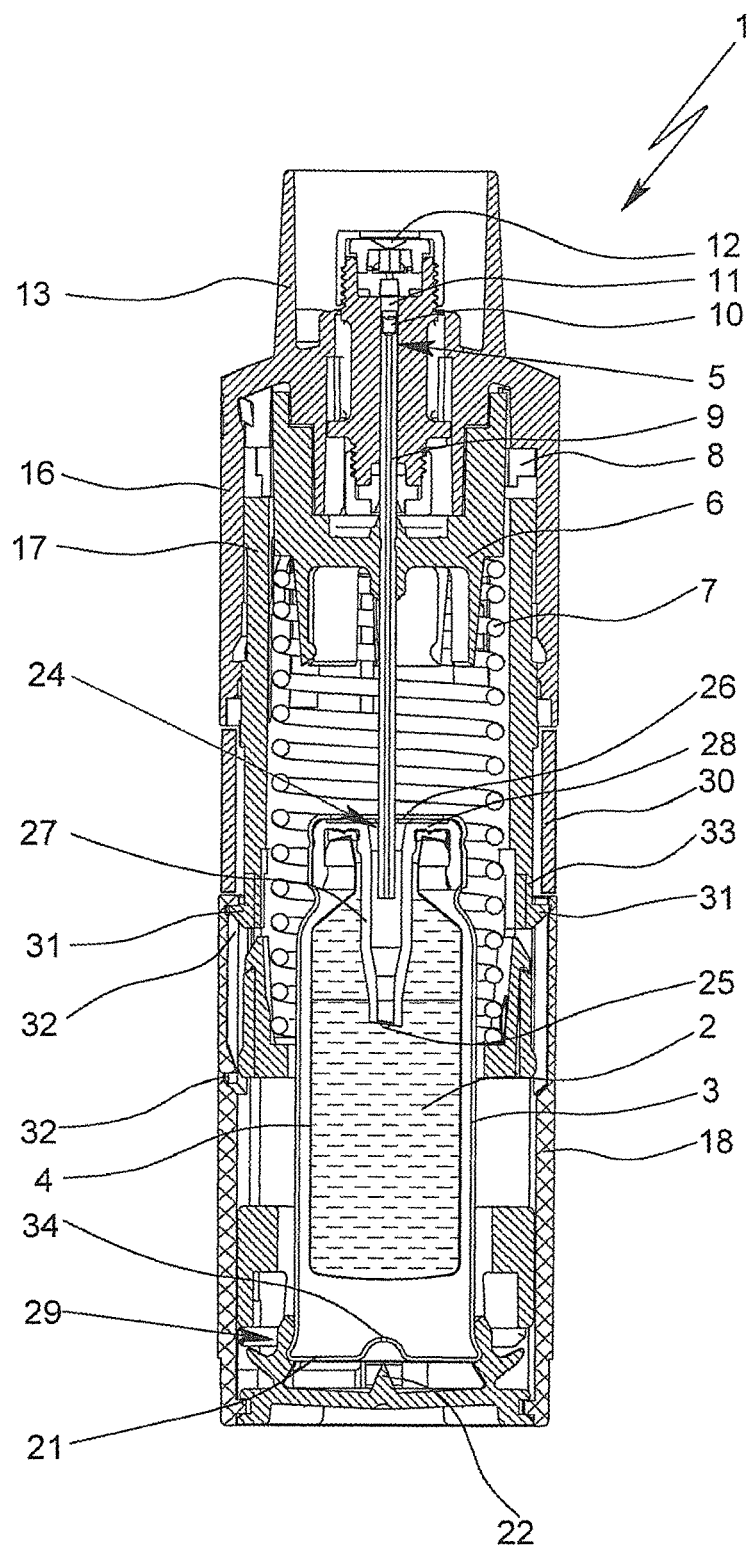
Figure 4:
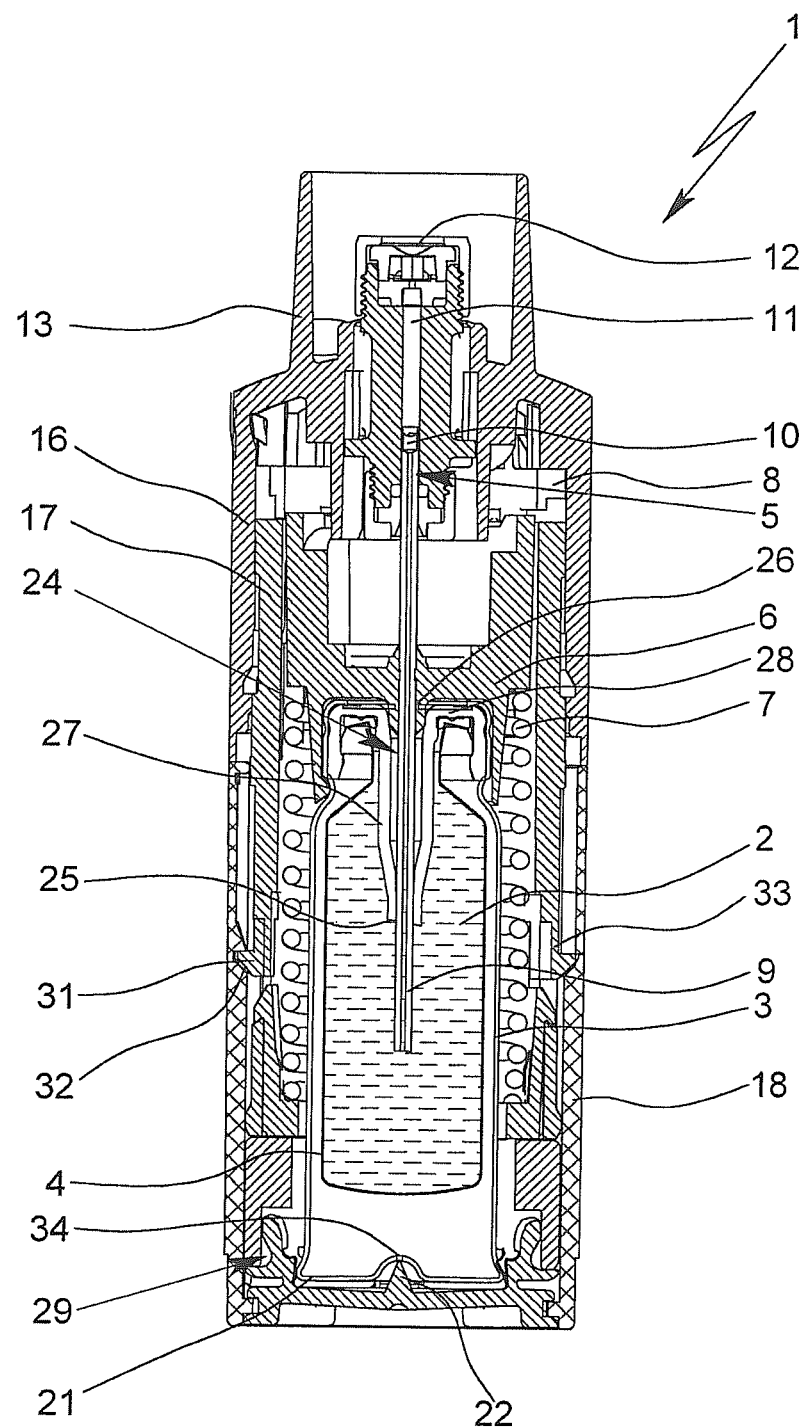
Figure 5:
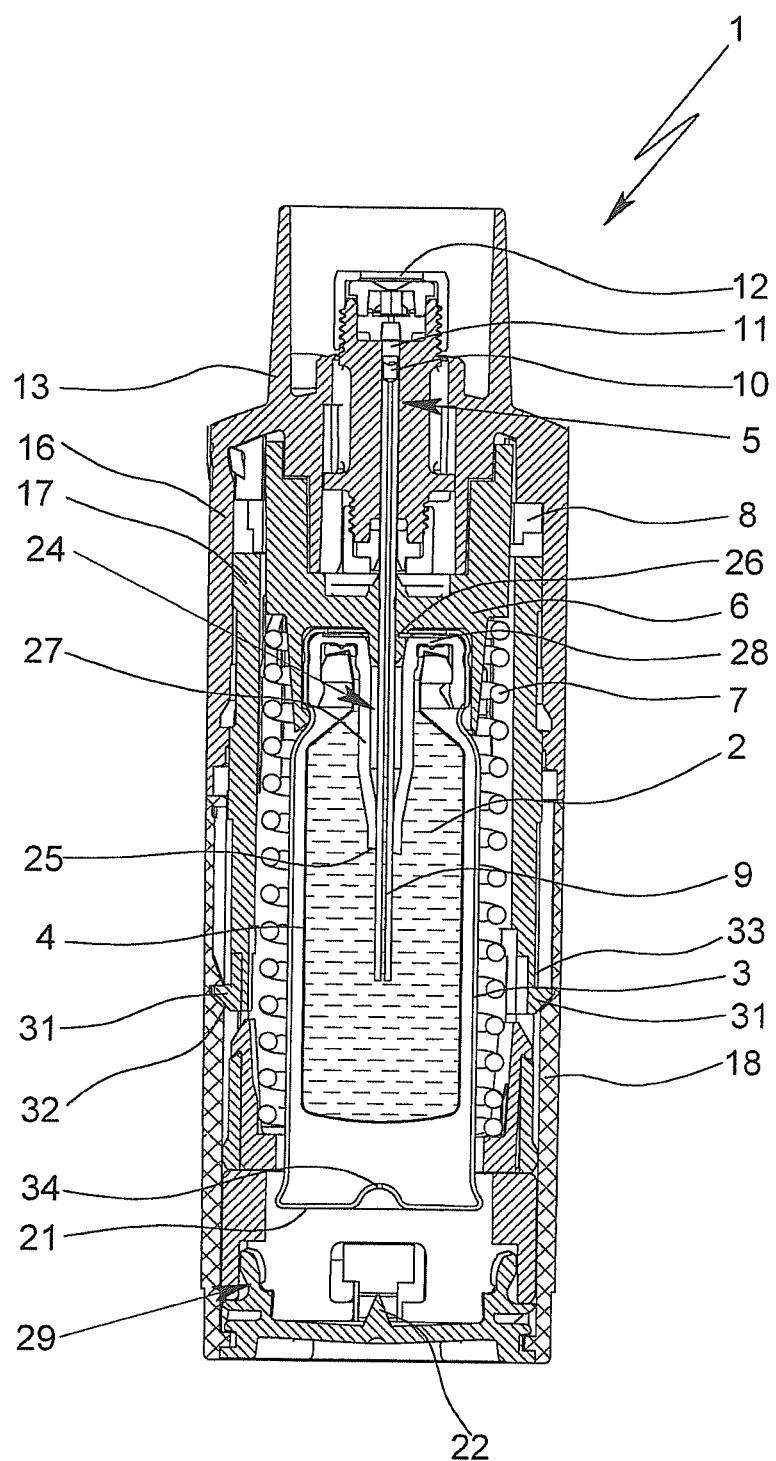
Figure 6:
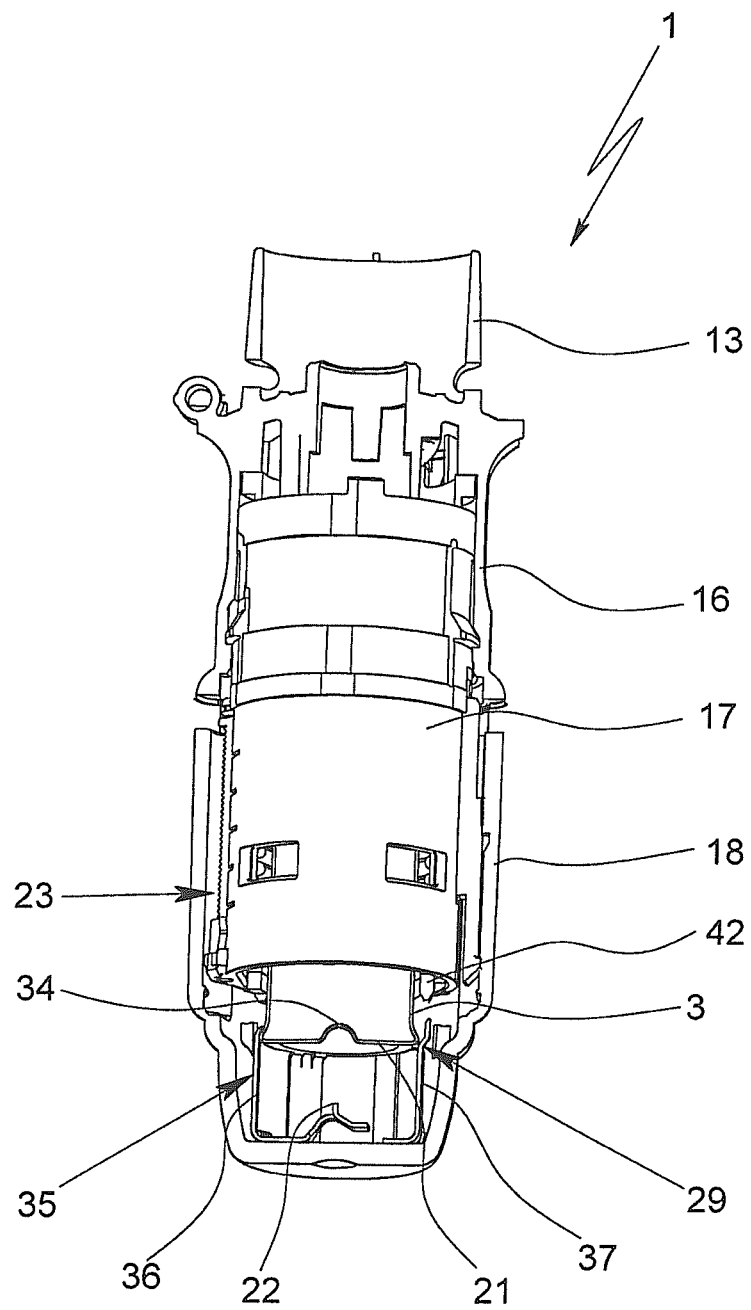
Figure 7:
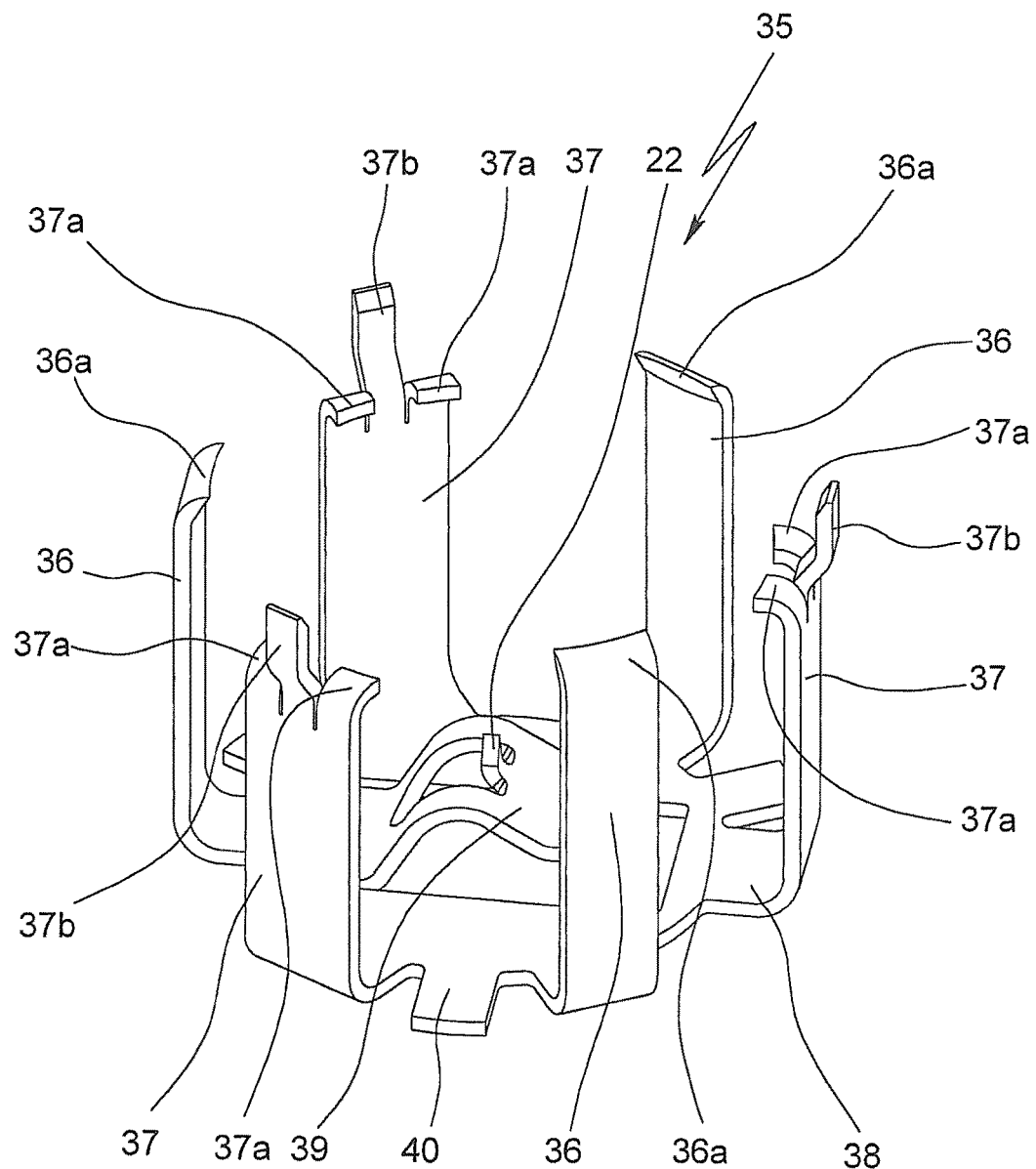
Figure 8:
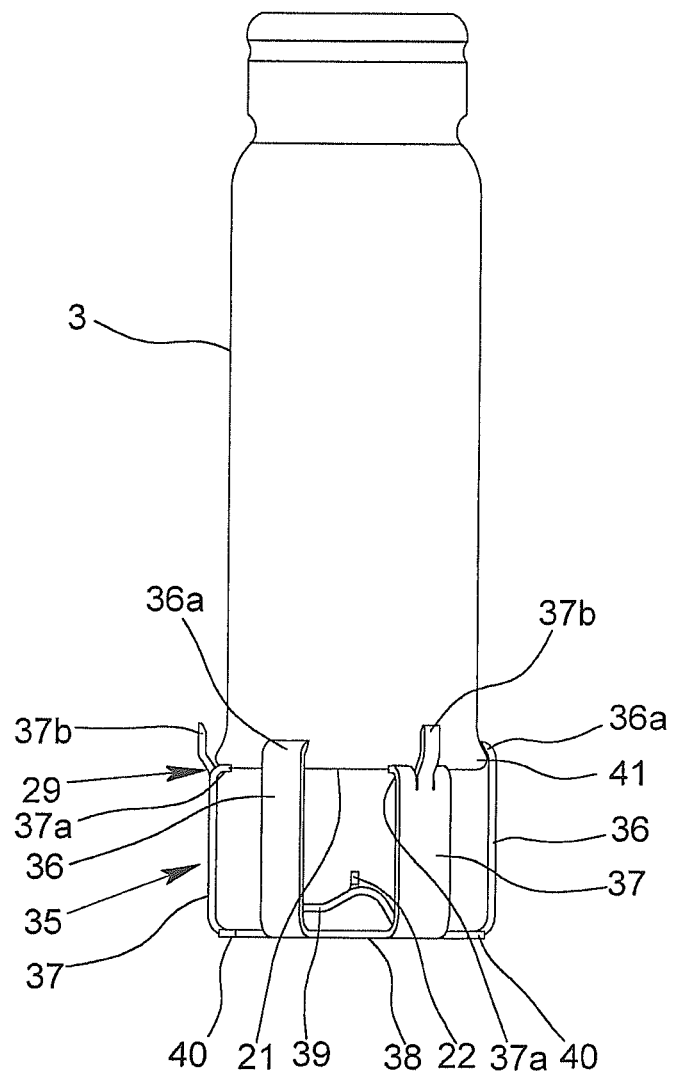
Figure 9:
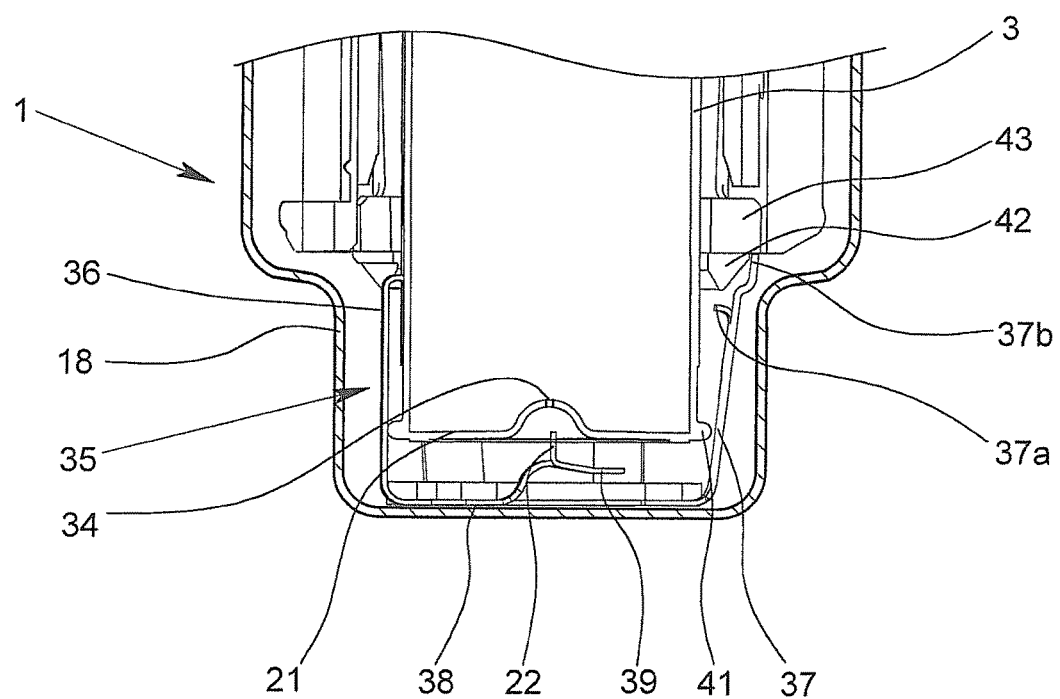
Figure 10:
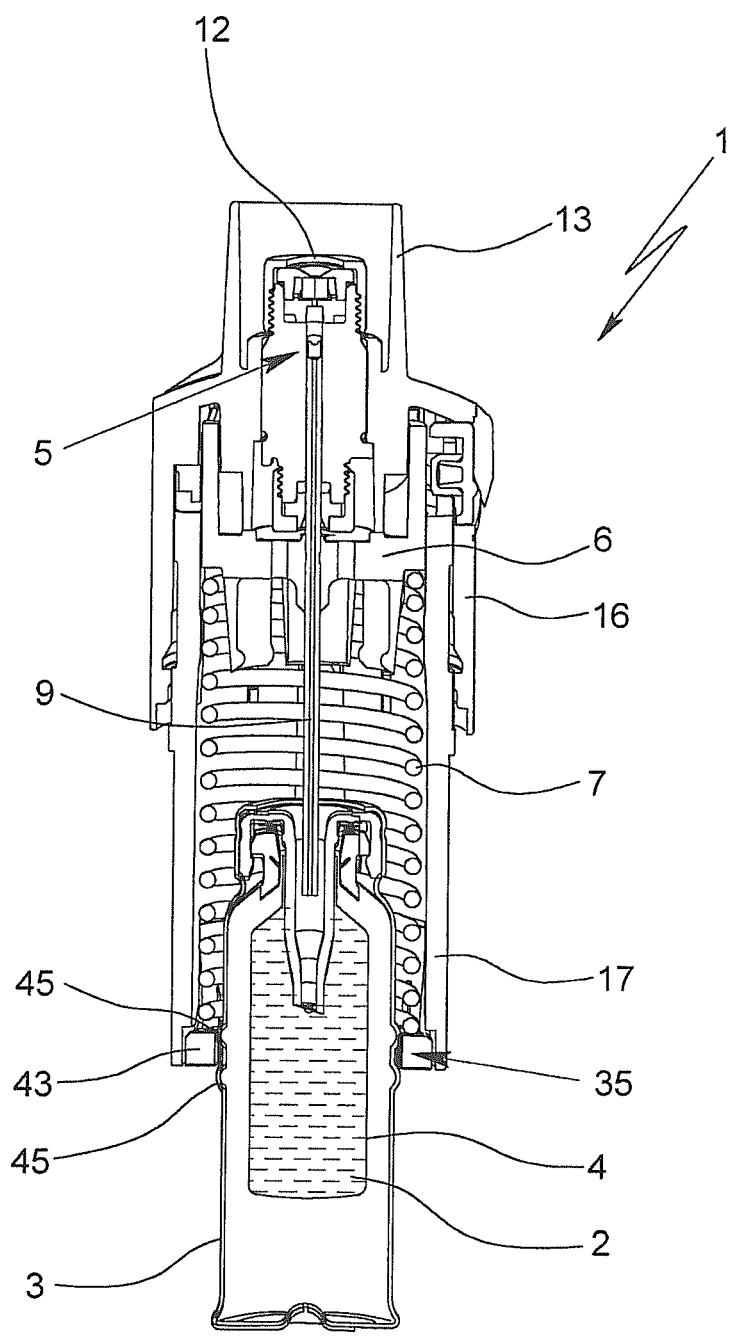
Figure 11:
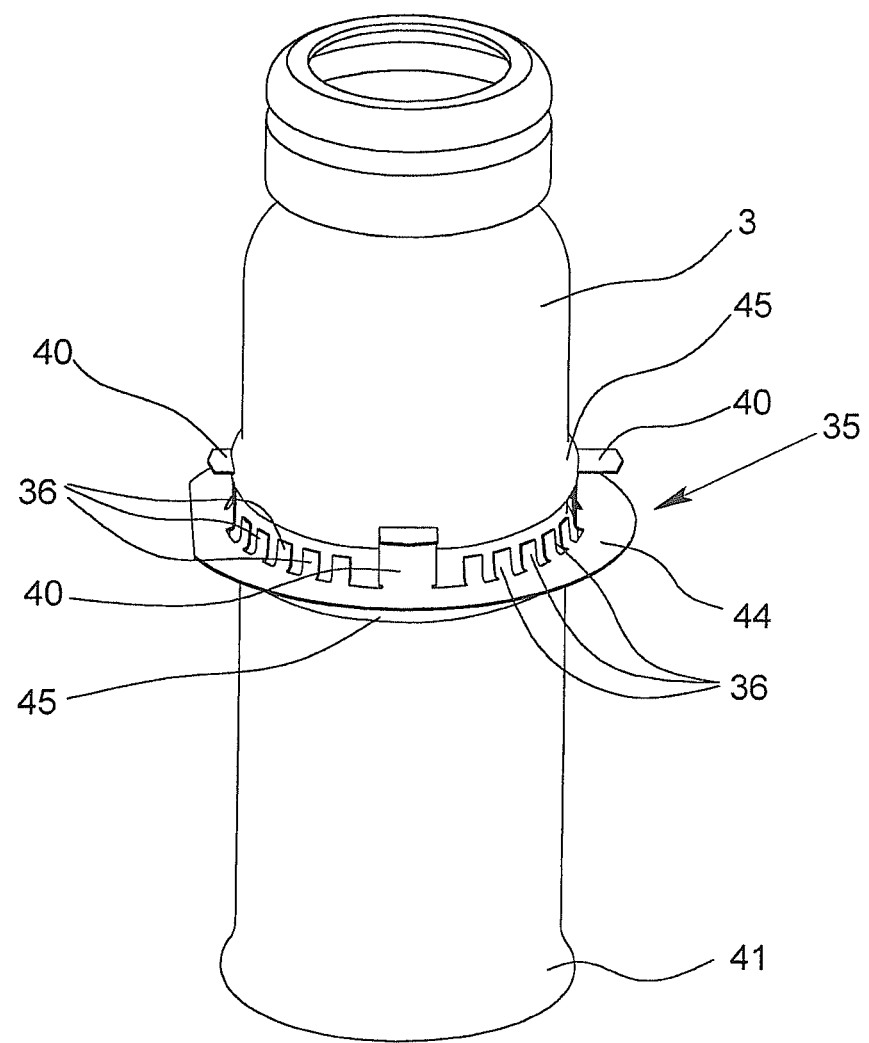
Figures 12, 13:
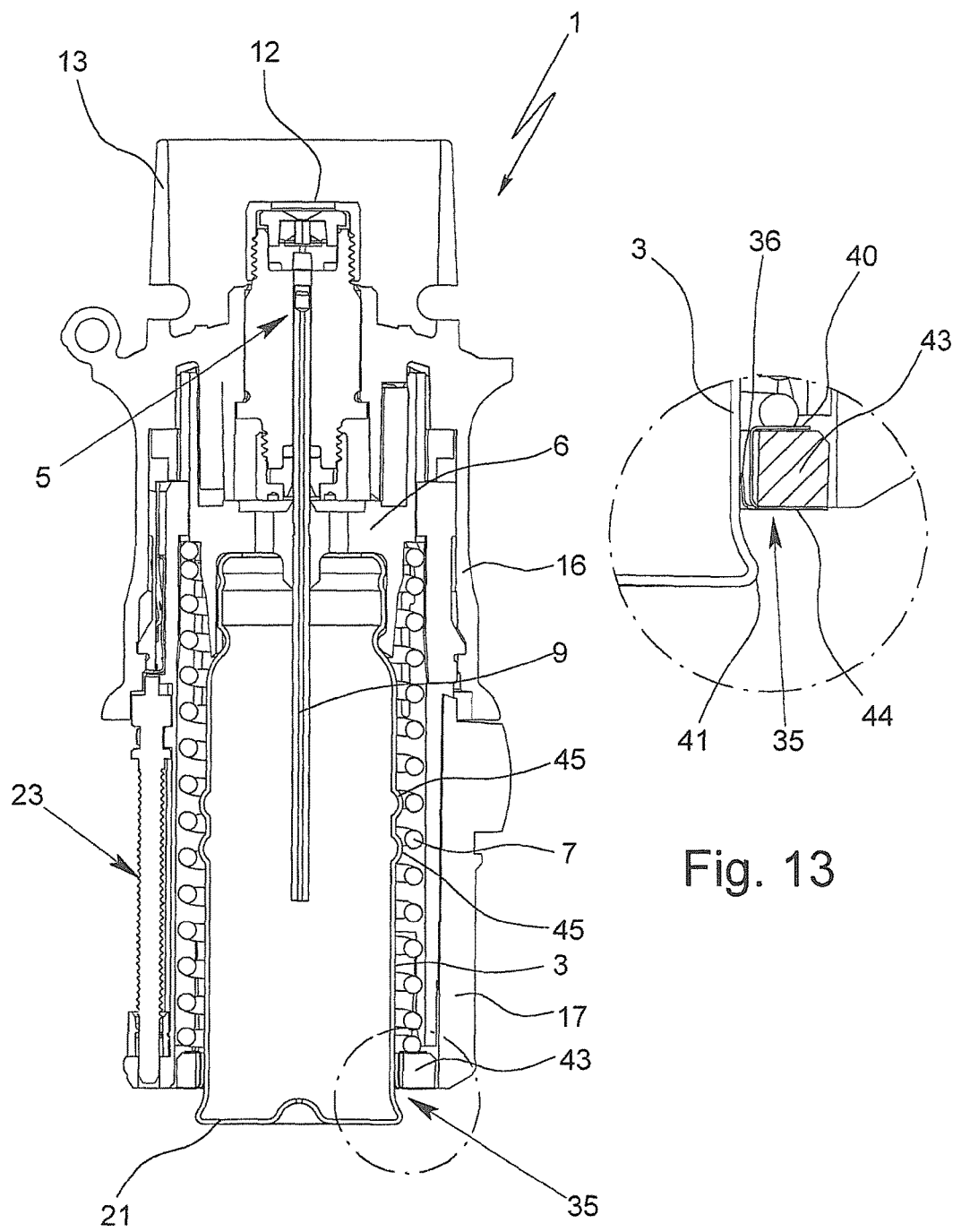

Further advantages, features, characteristics and aspects of the present invention will become apparent from the claims and the following description of preferred embodiments with reference to the drawings. It shows:

FIG. 1 a schematic section of a known nebulizer in a non-tensioned state;

FIG. 2 a schematic section, rotated through 90° compared with FIG. 1, of the known nebulizer in a tensioned state;

FIG. 3 a schematic section of a nebulizer in a delivery state with a partly closed housing and with a pre-installed, closed container;

FIG. 4 a schematic section of the nebulizer according to FIG. 3 in an activated, tensioned state with the completely closed housing and with the opened container;

FIG. 5 a schematic section of the nebulizer according to FIG. 4 in a non-tensioned state;

FIG. 6 a schematic section of a nebulizer according to a first embodiment of the present invention with a partly closed housing and with a securing means in a housing part holding unmoveably a container in the nebulizer;

FIG. 7 a perspective view of the securing means;

FIG. 8 a side view of the securing means holding the associated container unmoveably;

FIG. 9 a schematic partial view of a part of the nebulizer with opened securing means so that the container can move;

FIG. 10 a schematic section of a nebulizer according to a second embodiment of the present invention in a delivery state without lower housing part;

FIG. 11 a perspective view of the container of the nebulizer according to FIG. 10 with an associated securing means;

FIG. 12 a schematic section of the nebulizer according to FIG. 10 in the activated, non-tensioned state; and FIG. 13 a partial enlarged view of FIG. 12.

In the Figures, the same reference numerals have been used for identical or similar parts, resulting in corresponding or comparable properties and advantages, even if the associated description is not repeated.

FIGS. 1 and 2 show a known nebulizer 1 for atomizing a fluid 2, particularly a highly effective pharmaceutical composition or the like, diagrammatically shown in a non-tensioned state (FIG. 1) and in a tensioned state (FIG. 2). The nebulizer 1 is constructed in particular as a portable inhaler and preferably operates only mechanical and/or without propellant gas.

When the fluid 2, preferably a liquid, more particularly a pharmaceutical composition, is nebulized, an aerosol 14 (FIG. 1) is formed, which can be breathed in or inhaled by a user.

Usually the inhaling is done at least once a day, more particularly several times a day, preferably at set intervals, depending on the complaint or illness from which the patient is suffering.

The nebulizer 1 is provided with or comprises an insertable container 3 containing the fluid 2. The container 3 thus forms a reservoir for the fluid 2 which is to be nebulized. Preferably, the container 3 contains an amount of fluid 2 or active substance which is sufficient to provide up to 200 dosage units, for example, i.e. to allow up to 200 sprays or applications. A typical container 3, as disclosed in WO 96/06011 A1, holds e.g. a volume of about 2 to 10 ml.

The container 3 is substantially cylindrical or cartridge-shaped and once the nebulizer 1 has been opened the container can be inserted therein from below and changed if desired. It is preferably of rigid construction, the fluid 2 in particular being held in a collapsible bag 4 in the container 3.

The nebulizer 1 comprises preferably a pressure generator 5 for conveying and nebulizing the fluid 2, particularly in a preset and optionally adjustable dosage amount. The pressure generator 5 comprises preferably a holder 6 for the container 3, an associated drive spring 7, only partly shown, a locking element 8 which can be manually operated to release the spring 7, a conveying element, such as a conveying tube 9, a non-return valve 10, a pressure chamber 11 and/or an nozzle 12 for nebulizing the fluid 2 into a mouthpiece 13. The container 3 is fixed or held in the nebulizer 1 via the holder 6 such that the conveying tube 9 penetrates into the container 3. The holder 6 may be constructed so that the container 3 can be exchanged.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10 (conveying of the fluid 2, suction stroke). Then, the nebulizer 1 is in the so-called activated or tensioned state.

During the subsequent relaxation after actuation of the locking element 8 the fluid 2 in the pressure chamber 11 is put under pressure as the conveying tube 9 with its now closed non-return valve 10 is moved back upwards by the relaxation of the drive spring 7 and now acts as a pressing ram or piston (pressure generation and/or nebulization). This pressure forces the fluid 2 through the nozzle 12, whereupon it is nebulized into the aerosol 14, as shown in FIG. 1.

Generally, the nebulizer 1 operates with a spring pressure of 5 to 200 MPa, preferably 10 to 100 MPa on the fluid 2, with a volume of fluid 2 delivered per stroke of 10 to 50 μl, preferably 10 to 20 μl, most preferably about 15 μl. The fluid 2 is converted into or nebulized as aerosol 14 the droplets of which have an aerodynamic diameter of up to 20 μm, preferably 3 to 10 μm. Preferably, the generated jet spray has an angle of 20° to 160°, preferably 80° to 100°. These values also apply to the nebulizer 1 according to the teaching of the present invention as particularly preferred values.

A user (not shown) can inhale the aerosol 14, while an air supply can be sucked into the mouthpiece 13 through at least one air supply opening 15.

Preferably, the nebulizer 1 can be manually activated or tensioned. The nebulizer 1 comprises preferably an upper housing part 16 and an inner part 17 which is rotatable relative thereto (FIG. 2) having an upper part 17*a* and a lower part 17*b* (FIG. 1), while an in particular manually operable (lower) housing part 18 is releasable fixed, particularly fitted onto the inner part 17, preferably by means of a retaining element 19. Preferably, the housing parts 16 and 18 form a housing of the nebulizer 1. In order to insert and/or replace the container 3 the housing part 18 can be detached from the nebulizer 1 or its housing.

The housing part 18 can be rotated relative to the upper housing part 16, carrying with it the part 17*b* of the inner part 17. As a result the drive spring 7 is tensioned in the axial direction by means of a gear or transmission (not shown) acting on the holder 6. During tensioning the container 3 is moved axially downwards until the container 3 assumes an end position as shown in FIG. 2. In this activated or tensioned state the drive spring 7 is under tension. During the nebulizing process the container 3 is moved back into its original position (non-tensioned position or state shown in FIG. 1) by the drive spring 7. Thus the container 3 executes a lifting or stroke movement during the tensioning process and during the atomizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an aeration means, such as an axially acting spring 20 arranged in the housing part 18, comes in contact with base 21 of the container 3 and pierces the container 3 or a base seal thereon with a piercing element 22 when the container 3 makes contact with it for the first time, to allow air in or aeration.

The nebulizer 1 may comprise a monitoring device 23 which counts the actuations of the nebulizer 1, preferably by detecting the rotation of the inner part 17 relative to the upper part 16 of the housing. Preferably, the monitoring device 23 blocks the actuation or use of the nebulizer 1, e.g. blocks the actuation of the locking element 8, when a certain number of actuations or discharged doses has been reached or exceeded.

A preferred construction and mode of the inhaler or nebulizer 1 will now be described in more detail with reference to FIGS. 3 to 5, but emphasizing only essential differences from the nebulizer 1 according to FIGS. 1 and 2. The remarks relating to FIGS. 1 and 2 thus apply preferably accordingly or in a similar manner, while any desired combinations of features of the nebulizer 1 according to FIGS. 1 and 2 and the nebulizer 1 described below are possible.

FIGS. 3 to 5 show, in schematic sectional views, a nebulizer 1 according to a preferred embodiment of the present invention. FIG. 3 shows the nebulizer 1 in a delivery state, i.e. with pre-installed container 3 which is still closed. In this state, the housing of the nebulizer 1 is not completely closed, in particular the housing part 18 is not completely pushed on the inner part 17. FIGS. 4 and 5 show the nebulizer 1 in an activated and/or tensioned state with the housing completely closed and with the container 3 opened. In FIG. 4, the nebulizer 1 or drive spring 7 is tensioned, i.e. the container 3 is in its lower position. FIG. 5 shows the nebulizer 1 in a non-tensioned state, e.g. after the delivery or discharge of one dose of the fluid 2; the container 3 is in its upper position.

The container 3 is already mounted or pre-installed in the nebulizer 1 in the delivery state, as shown in FIG. 3. In this state, the container 3 is still closed, i.e. there is no fluidic connection between the container 3 or its bag 4 on one hand and the nebulizer 1 or its pressure generator 5 or the conveying element on the other hand.

The container 3 comprises a fluid outlet 24 for outputting the fluid 2 to be dispensed. In particular, the fluid outlet 24 allows a fluidic connection between the container 3 or its bag 4 on one hand and the nebulizer 1, its pressure generator 5 or the conveying element on the other hand.

The fluid outlet 24 has an inner closure 25 that is preferably formed by a septum, a membrane, a plastic seal or the like and/or is provided inside the container 3. Optionally, a second or outer closure 26 can be provided.

Preferably, the closures 25 and 26 are designed such that successive opening is possible by means of one common element, in particular the conveying element or conveying tube 9 or the like, and/or by piercing.

In the preferred embodiment, the first closure 25 and second closure 26 are arranged one after the other and/or spaced in axial direction or direction of the stroke movement of the container 3 or with respect to the main outlet direction of the fluid 2.

Generally, the container 3, fluid outlet 24 or closures 25 or 26 are opened in particular by means of a conveying element, such as the conveying tube 9, or the like and/or by piercing or in any other suitable manner. In particular, the opening is achieved by moving the container 3 relative to the nebulizer 1 or conveying element or tube 9 or the like and/or by movement in longitudinal or axial direction.

Preferably, the first or inner closure 25 is formed or supported by a closure part 27 extending from the outlet or head end of the container 3 into the container 3 or bag 4. The second or outer closure 26 is preferably located adjacent to the head or axial end of the container 3 and/or held or connected to a flange 28, which can be formed by the closure part 27 or any other suitable part. However, other constructional solutions are possible.

In the delivery state according to FIG. 3, the container 3 has been pre-installed, i.e. inserted into the nebulizer 1. However, the container 3 or its fluid outlet 24 is not yet opened. In particular, the second closure 26 is already opened, but not the first closure 25. This is achieved in particular in that the housing of the nebulizer 1 is closed only partly, i.e. not completely, in the delivery state, preferably by not completely closing or pushing on the housing part 18 in the shown embodiment. Preferably, the housing part 18 is snapped on or inserted only partly in the delivery state.

In particular, the container 3 is attached to or held by or secured in the housing part 18, in particular by a transportation lock 29, which is preferably arranged within or at the housing part 18. The transportation lock 29 holds the container 3 preferably temporarily, in particular before attaching the housing part 18 to the nebulizer 1 and/or in the delivery state. In particular, the transportation lock 29 holds the container 3 fixed during the fluidic connection of container 3 and/or during the mechanic connection of container 3, here with holder 6. Preferably, the transportation lock 29 holds the container 3 fixed during opening, in particular piercing, the container 3.

In the delivery state, in which the nebulizer 1 can be shipped or delivered to the user or is still packed, the nebulizer 1 or the housing part 18 is preferably secured, in particular by means of a securing member 30, such that the container 3 and/or housing part 18 are held sufficiently spaced from the nebulizer 1 or upper housing part 16 and/or prevented from being completely inserted or pushed on the conveying element or tube 9, the housing or inner housing part 17 or the like and/or such that (complete) opening of the container 3, namely of the first closure 25, is prevented.

In the shown embodiment, the securing member 30 is preferably mounted between the housing part 18 and the upper housing part 16 and preferably engages with or between the housing parts 16 and 18, so that the housing part or lower part 18 is axially secured or is kept or held sufficiently away or spaced from the upper housing part 16 to be able to hold the (still) closed container 3 or first closure 25 away from the conveying tube 9.

In the preferred embodiment, the securing member 30 is at least substantially hollow and/or cylindrical and is disposed axially between the (lower) housing part 18 and the upper housing part 16. To activate the nebulizer 1 or prepare it for use, i.e. to push the housing part 18 fully on in the axial direction and thereby open the container 3, the securing member 30 first has to be removed or released or opened. In the shown preferred embodiment, the securing member 30 is constructed in the manner of a banderole or the like, made of plastics, for example, and/or can be manually opened, removed or destroyed. The securing member 30 may alternatively or simultaneously form or constitute a seal of origin. However, other embodiments of the securing member 30 are also possible, e.g. in the form of a security tag or the like.

Preferably, the container 3 and/or housing part 18 are held positively or in a form-fit or interlocking manner in the delivery state. This is achieved in the preferred embodiment in particular by means of the transportation lock 29 acting between the container 3 and the housing part 18, and the securing member 30 acting between the housing part 18 and the housing of the nebulizer 1 or the upper housing part 16 or the like. However, the transportation lock 29 or securing member 30 could also act directly between the container 3 on one hand and the nebulizer 1, its housing, the upper housing part 16, the inner housing part 17 or the holder 6 on the other hand.

In the non-activated position, the housing part 18 is preferably secured so that it cannot be lost and, in particular, cannot be released. Then, the housing or lower part 18 of the nebulizer 1 can no longer be detached from the nebulizer 1 after it has been (partially) axially pushed on for the first time, i.e. the nebulizer 1 cannot be opened any longer, with the result that that the container 3 cannot be changed, i.e. cannot be removed again.

In order to secure the housing part 18, it is preferably held or latched positively or in an interlocking or form-fit manner. Preferably, the housing part 18 is secured by means of at least one latching lug 31, protrusion, nose or the like which engages in an associated latching recess 32 in the housing part 18 or the like and, thereby, secures the housing part 18 against axial removal by interlocking engagement. In the present embodiment, the latching lug 31 may be formed by or at a latching arm 33 which can preferably flex. Thus, a ratchet-like means for securing the housing part 18 to the nebulizer 1 or its housing or the upper housing part 16 is formed. However, other constructional solutions are also possible.

Once the security member 30 has been removed a user (not shown) can push the housing part 18 fully on in the axial direction and thereby open the container 3, i.e. first closure 25, by inserting the conveying element or conveying tube 9. FIGS. 4 and 5 show this activated state with the housing part 18 pushed fully on and/or the container 3 open (fluidically connected to the nebulizer 1 or its pressure generator 5 or the conveying element or tube 9). In this pushed on or activated state, the housing part 18 is preferably secured or axially fixed again by interlocking engagement, i.e. form-fit manner in axial direction, particularly by the engagement of the latching arm 33 or latching lug 31 in a corresponding further latching recess 32 or by means of some other mechanical securing device.

FIG. 4 shows the nebulizer 1 or container 3 in the activated state, the container 3, i.e. first closure 25, is open, i.e. the container 3 or its fluid 2 is fluidically connected to the nebulizer 1 or its pressure generator 5, and the housing part 18 has been pushed fully on in the axial direction. In order to bring the holder 6 into (complete) engagement with the container 3 at the head end and then be able to move the container 3 back and/or forth for the suction/tensioning and pressing strokes, it may be necessary to tension the nebulizer 1 or it drive spring 7 for the first time.

During this tensioning process the holder 6 is moved together with the conveying tube 9 axially towards or into the housing part 18, thus bringing the holder 6 into (complete) engagement with the container 3 and preferably also moving or pressing the container 3 against the piercing element 22 in the region of the base of the housing part 18 and thereby piercing or opening a venting hole 34 in the container base 21. FIG. 4 shows the nebulizer 1 in this tensioned and activated state. The holder 6 is engaged with the container 3 and the conveying tube 9 has been fully inserted into the container 3.

FIG. 5 shows the nebulizer 1 in the relaxed, non-tensioned state, i.e. after atomization or discharge of a dose of the fluid 2. The holder 6 and the container 3 are in the upper position. The holder 6 is still engaged with the container 3 and remains engaged during the further uses of the nebulizer 1. Further, the container 3 is still open and fluidically connected, i.e. the nebulizer 1 remains activated.

The nebulizer 1 is activated after the removal of the securing member 30 and (total) axial pushing on of the housing part 18 and can be used in the same way as the nebulizer 1 shown in FIGS. 1 and 2. The pre-installation of the container 3 prevents the wrong container 3 or used containers 3 from being inserted in the nebulizer 1 by the user.

As preferably the container 3 cannot then be removed, especially because the nebulizer 1 cannot be opened and the housing part 18 cannot be removed again, undesirable replacement of the container 3 by the user and in particular undesirable interim or subsequent opening of the nebulizer 1 by the user can be prevented.

To prevent unwanted opening of the container 3, particularly of the first closure 25, in the delivery state of the nebulizer 1, preferably the transportation lock 29 is provided. By frictional, forcible or interlocking engagement, for example, the transportation lock 29 prevents the container 3 from undesirably moving axially in the nebulizer 1, e.g. during transportation, in the event of accidental dropping of the nebulizer 1 or the like.

Preferably, the opening of the transportation lock 29 occurs automatically when closing the nebulizer 1 or its housing completely, i.e. when snapping or pushing on the housing part 18 completely towards the upper housing part 16. During this (axial or telescopic) closing movement, the transportation lock 29 is opened and the container 3 released in axial direction preferably only in a last part of the movement and/or just little before the final completely closed position is reached or just when the final completely closed position is reached.

The closing movement of the nebulizer 1 opens the transportation lock 29 preferably automatically. In particular, the transportation lock 29 is opened by the direct or indirect interaction with or actuation by the housing of the nebulizer 1, the inner part 17 or its lower part 17b, a holding ring 38 bearing the spring 7 or the like. Preferably, the container 3 and/or first closure 25 are opened as well as the transportation lock 29 by means of a common actuation, here the closing movement of the nebulizer 1 or its housing or bottom part 18.

FIGS. 4 and 5 show the transportation lock 29 in the open position, i.e. wherein the container 3 is free to move axially.

Preferably, in the non-activated state, i.e. when the housing part 18 has not been pushed on fully, the nebulizer 1 may be locked to prevent tensioning of the pressure generator 5, i.e. in particular to prevent rotation of the inner part 17 relative to the upper housing part 16. This may be important when the nebulizer 1 is supplied in the delivery state with the pressure generator 5 not under tension. Accordingly, the inhaler 1 may have a barrier, so that the inner part 17 can only be rotated relative to the upper housing part 16 when the housing part 18 has been pushed fully on. Alternatively or additionally, the securing member 30 may block not only pushing on of the bottom part 18 in the delivery state, but also any rotation of the inner part 17 until the securing member 30 has been opened, released or removed.

In the following, a first embodiment of the inhaler or nebulizer 1 according to the present invention will be described in detail with reference to FIGS. 6 to 9, wherein only essential differences will be emphasized so that the previous remarks and explications relating to the nebulizers 1 according to FIGS. 1 to 5 apply preferably in a corresponding or similar manner.

FIG. 6 shows in a very schematic, partially sectional view the nebulizer 1 according to the first embodiment of the present invention. The nebulizer 1 is shown a transitional state from the delivery state to the activated state with not completely closed housing or housing part 18. The housing part 18 has already been pushed on the inner part 17 more than initially provided in the delivery state such as shown in FIG. 3. Therefore, the container 3 has already been opened in the state shown in FIG. 6. Further, the securing member 30, which preferably secures the housing part 18 in the delivery state against pushing on the inner part 17, has already been released or opened or removed in the state shown in FIG. 6.

The nebulizer 1 or its housing comprises a securing means 35 for holding the container 3 such that the container 3 is moveable back and forth for the conveying of the fluid 2, pressure generation and/or nebulization, but is inseparable from the housing or housing part 18, and/or such that the container 3 is unmoveably held in the delivery state of the nebulizer 1.

The securing means 35 is located or arranged preferably at or in the housing part 18 as shown in FIG. 6.

FIG. 7 shows in a perspective view a preferred embodiment of the securing means 35. FIG. 8 shows the securing means 35 connected with the container 3.

Preferably, the securing means 35 comprises or consists of a metal and/or stamping part and/or consists of a single, unitary part as shown in FIG. 7.

Preferably, the securing means 35 is made of steel, in particular spring steel.

Preferably, the securing means 35 is produced from sheet material by cutting, stamping or the like and/or by bending.

Preferably, the securing means 35 or the part forms a cage, in particular, encompasses the container 3 or an end portion thereof.

Preferably, the securing means 35 comprises holding elements 36 and/or locking elements 37. The elements 36 and 37 are preferably designed like arms, fingers leaves or the like. In particular, the elements 36, 37 are alternately distributed over a circumference of the container 3 and/or extend at least essentially axially or in the direction of the back and forth movement of the container 3.

Preferably, the elements 36 and 37 are held by or connected with a base 38 of the securing means 35.

Preferably, the securing means 35 or base 38 comprises or holds the piercing element 22 for piercing the container 3, i.e. opening the container base 21 or its venting hole 34 in the activated and tensioned state, i.e. when the container 3 reaches its lower end position. In the shown embodiment, the piercing element 22 is formed by a respective bending of a spring portion 39 of the securing means 35 or its base 38. The spring portion 39 can support or facilitate the (complete or final) connection of the container 3 to holder 6.

The securing means 35 or base 38 comprises preferably at least one or multiple fixing portions 40 for fixing the securing means 35 at or in the nebulizer 1 or housing or housing part 18. In particular, the fixing portions 40 may fix the securing means 35 when the securing means 35 is pressed into the housing part 18 by cooperating with the side wall of the housing part 18.

However, it is also possible to overmold the securing means 35, its base 38, the fixing portions 40 or the like. Moreover, the securing means 35 could be connected with the housing part 18 or the like in any other suitable manner.

Preferably, the securing means 35 does not only prevent the separation of the container 3 from the nebulizer 1, its housing or housing part 18, but also forms the transportation lock 29 for holding the container 3 unmovable in the housing in the delivery state of the nebulizer 1. FIGS. 6 and 8 shows this state or situation when the container 3 is held (axially) unmovable by the securing means 35, i.e. when the transportation lock 29 is closed. In this situation, the container 3 or its preferably radially protruding end or edge 41 of the container 3 is held between the holding element 36 and locking element 37, in particular between respectively formed or bent ends of the elements 36 and 37.

In the shown embodiment, the container end or edge 41 is caught between end portions 36a and 37a of the elements 36 and 37. The holding elements 36 grip or extend over the edge 41 and the locking elements 37 or its end portions 37a grip or extend under the edge 41 or container base 21 so that the edge 41 and container 3 are securely held preventing any axial movement of the container 3 relative to the securing means 35 and relative to the associated housing part 18 in this state, i.e. with locked securing means 35/transportation lock 29.

The holding element 36 and the locking elements 37 are distributed alternatingly around the container 3 or edge 41.

Preferably, the end portions 36a of the holding elements 36 end in a first radial plane and the end portions 37a of the locking elements 37 end in another, second radial plane, wherein the two planes are axially offset to hold the edge 41 in between and/or wherein the second plane is located axially between the first plane and the lower end position of the container 3 or the lower end of the housing part 18 or the piercing element 22. Additionally or alternatively, the end portions 36a end on another radius (outer radius) than the end portions 37a and/or are axially spaced therefrom.

The end portions 36a and/or 37a are preferably form like claws or the like and/or extend preferably radially inwardly.

Preferably, the elements 36 and/or 37 can flex with its free ends radially outwardly.

For example, the ends of the end portions 36a may be inclined such that the container 3 may be inserted into or connected with the securing means 35 by a respective axial force so that the holding elements 36 flex outwardly to allow passing of edge 41. However, the holding elements 36 can be flexed outwardly also by a suitable tool (not shown) or the like when the container 3 is inserted, in particular with its edge 41, into the securing means 35.

Preferably, the holding elements 36 prevent separation of the container 3 from the securing means 35 and, thus, from the associated housing part 18 or the like.

The locking elements 37 or its end portions 37a can be flexed radially outwardly in order to open the axial holding or transportation lock 29 (this will be explained in detail with reference to FIG. 9 in the following). Then, the container 3 can axially move, in particular back and forth and/or with its edge 41 between the first plane and the piercing element 22 in the present embodiment.

In the present embodiment, the locking elements 37 comprise actuation portions 37b (preferably formed at the free ends and/or between adjacent end portions 37a). Preferably, the actuation portions 37b form axial extensions which may be radially offset. The actuation portion 37b cooperate with an associated control member 42 or multiple control members 42 of the nebulizer 1 such that the locking elements 37 are flexed radially outwardly when (completely) closing the housing to open the transportation lock 29 (here primarily formed by the locking elements 37 or its end portions 37a).

FIG. 6 shows schematically the control member 42 axially spaced from the associated actuation portion 37b as the housing has not yet been closed (completely).

FIG. 9 shows a lower part of the completely closed nebulizer 1 with opened transportation lock 29, i.e. with radially outwardly flexed locking elements 37. FIG. 9 shows that the control member 42 has an inclined guiding surface or the like to convert the axial closing movement into the radial opening movement of the actuation portion 37b and, thus, of the associated locking element 37 to open the transportation lock 29, in particular when the housing has been completely closed or when the housing part 18 has been pushed completely on the nebulizer 1.

The control member 42 is preferably formed as an axial protrusion. It can be formed by or at a ring 43 or any other bearing means of the nebulizer 1 for counter-bearing the drive spring 7 in the inner part 17 or by or at any other suitable component if the nebulizer such as the inner part 17.

The control member 42 may be formed like an axial protruding ring or shoulder or ridge which extends along the ring 43.

The control member 42 may additionally secure the holding elements 36 against axial opening when the housing is completely closed as schematically shown in FIG. 9. In this case, the control member 42 contacts the holding element(s) 36 or its end portions 36a peripherally on the outer side to prevent any outward flexing. Then, the securing means 35 or its holding elements 36 are secured against opening so that the container 3 is securely held within the securing means 35 or the cage formed by the securing means 35 or holding elements 36.

FIG. 9 shows the container 3 in its lower position when the piercing element 22 can pierce the venting hole 34 or an associated seal attached to the container base 21.

In the present embodiment, the securing means 35 has multiple functions. It holds the container 3 (in the activated state/with completely closed housing) such that it can move back and forth, in particular during conveying of the fluid 2, during pressure generation and/or during nebulization, wherein the container 3 is inseparable from the housing or the housing part 18. Further, the securing means 35 forms the transportation lock 29 and/or holds the container 3 unmovable in the delivery state of the nebulizer 1. Additionally or alternatively, the securing means 35 comprises an opening means, here the piercing element 22, for opening the venting hole 34 of the container 3.

Preferably, the securing means 35 forms a cage which cannot be separated from the container 3 after connecting it with the container 3.

The transportation lock 29 and the locking elements 37 are kept opened during the normal use of the nebulizer 1, in particular as long as the housing is (completely) closed. When the housing is opened, i.e. the housing part 18 is detached, the control member 42 may disengage from the actuation portions 37b so that the locking element 37 can close or flex inwardly again. Then, the locking elements 37 may grip with its end portions 37a over the edge 41 of the container 3 such that an additional lock is formed which prevents that the container 3 can be separated from the securing means 35/housing part 18.

The securing means 35 prevents separation of the container 3 from the housing part 18. Therefore, the container 3 can be replaced or exchanged only together with the housing part 18 if the housing part 18 can be detached from the nebulizer 1 or inner part 17 at all. However, it is also possible that the nebulizer 1 cannot be opened. Then, the container 3 cannot be replaced.

In the following, a second embodiment of the nebulizer 1 and the securing means 35 will be described with reference to FIGS. 10 to 13. The previous remarks and explications apply in a corresponding or similar manner. Only essential differences or new aspects of the second embodiment will be explained.

FIG. 10 shows in a schematic sectional section the nebulizer 1 according to the second embodiment in the delivery state. The housing part 18 is omitted.

In the second embodiment, the securing means 35 is arranged or located at or within the non-detachable part of the housing of the nebulizer 1, in particular at or in the upper housing part 16 or inner part 17. In particular, the securing means 35 is located or mounted at or within the ring 43 or any other suitable component preferably at the lower end of the inner part 17. In the shown embodiment, the securing means 35 is arranged at least primarily between the ring 43 and the container 3. However, other constructional solutions are possible.

FIG. 11 illustrates in a perspective view the container 3 and the associated securing means 35 in the delivery state. In the shown second embodiment, the securing means 35 forms an arrangement of multiple holding elements 36 which are preferably finger-like or leaf-like. The holding elements 36 are annularly arranged around a circumference of the container 3 and/or connected with a ring portion 44 of the securing means 35. In particular, the holding elements 36 are connected with the inner edge of the ring portion 44 and extend axially upwardly, i.e. in the direction of insertion of the container or into the nebulizer 1. The holding elements 36 are biased against the container 3 and/or inclined radially inwardly against the container 3.

The securing means 35 or securing ring formed by the ring portion 44 and the associated holding elements 36 in the shown embodiment comprises preferably fixing portions 40 for fixing the securing means 35 or securing ring at the nebulizer 1, its housing or inner part 17, in particular at the ring 43 counter-bearing the drive spring 7. The fixing portions 40 extend preferably in axial direction from the ring portion 44 and are angled radially outwardly at its free ends so that a form-fit engagement is possible with ring 43 (ring 43 is axially held between the ring portion 44 and the free ends of the fixing portions 40 in the preferred embodiment). Thus, the securing means 35 or securing ring can be securely fixed at the ring 43. However, other constructional solutions are possible as well.

It has to be noted that the securing means 35 or securing ring comprises or consists of a metal and/or stamping part and/or a single unitary part as already described with respect to the first embodiment.

The holding elements 36 of the securing means 35 or securing ring cooperate preferably with engagement means formed on or by the container 3 such that the container 3 is moveable back and forth but is inseparable from the housing or nebulizer 1, and/or such that the transportation lock 29 is formed and/or that the container 3 is (axially) unmoveably held in the delivery state of the nebulizer 1.

In the shown embodiment, the container 3 comprises at least one, here two radial shoulders, protrusions or corrugations 45 as engagement means. The corrugations 45 form preferably ring-like ribs or the like on the outer periphery of the container 3 and/or are axially spaced, in particular such that the holding elements 36 can engage in between the corrugations 45.

The engagement means or corrugations 45 are preferably arranged or formed on the container 3 such that the holding elements 36 engage—in particular in between the two corrugations 45 as schematically shown in FIGS. 10 and 11—in the delivery state such that the container 3 is held axially to avoid complete insertion of the container 3 and/or undesired opening of the container 3 or its first closure 25.

In particular, the upper corrugation 45 prevents that the container 3 can be detached from the nebulizer 1 because the holding elements 36 cannot overcome or move over this corrugation 45. Thus, the securing means 35 prevent replacement of the container 3 at all. In the opposite direction, the lower corrugation 45 forms an obstacle or resistance for the holding elements 36 so that the container 3 is secured against further insertion in the delivery state, i.e. this corrugation 45 forms together with the securing means 35 or its holding elements 36 the transportation lock 29). However, this obstacle or resistance can be overcome, i.e. the transportation lock 29 can be opened, by a sufficiently high force, e.g. by manually closing the housing or manually inserting the container 3, because the holding element 36 can flex radially outwardly so that the lower corrugation 45 can pass and the container 3 can be inserted further, i.e. can move upwardly in FIG. 10.

The corrugations 45 can differ in axial or circumferential location, form, radial extension, inclination, dimension or the like as required or desired, in particular to realize a secure holding of the container 3 in the delivery state, wherein the force is not too high which has to be overcome when the container 3 is further inserted and opened.

FIG. 12 shows the situation with the fully inserted container 3, i.e. the nebulizer 1 in the activated state (with opened transportation lock 29) with completely opened container 3. The container 3 is connected with holder 6. The drive spring 7 is not tensioned, i.e. the FIG. 12 shows the nebulizer in the non-tensioned state.

FIG. 13 shows a partial enlargement of the FIG. 12 in the area of the securing means 35. In this state, the container 3 can move essentially freely relative to the securing means 35 axially back and forth during the use of the nebulizer 2. However, the holding elements 36 will engage with the engagement means, here first with the lower corrugation 45, when it is tried to separate a container 3 from the nebulizer 1. The two corrugations 45 provide double security against separation of the container 3 after it has been inserted completely or after the securing means 35 or holding elements 36 have passed the lower corrugation 45.

Generally, it should be pointed out that in the proposed nebulizer 1 the container 3 can preferably be inserted, in the nebulizer 1. Consequently, the container 3 is preferably a separate component. However, the container 3 may theoretically be formed directly by the nebulizer 1 or part of the nebulizer 1 or may otherwise be integrated in the nebulizer 1.

As already mentioned, individual features, aspects and/or principles of the embodiments described may also be combined with one another as desired and may be used particularly in the nebulizer according to FIGS. 1 and 5 but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers, e.g. powder inhalers or so-called metered dose inhalers.

Preferably, the fluid 2 is a liquid, as already mentioned, especially an aqueous pharmaceutical formulation. However, it may also be some other pharmaceutical formulation, a suspension or the like.

According to an alternative embodiment the fluid 2 may also comprise particles or powder. In this case, instead of the expulsion nozzle 12, some other kind of supply device may be provided, especially an expulsion opening (not shown) or a supply channel (not shown) for supplying the fluid to or powder or the like into the mouthpiece 13. The optional air supply opening 15 then serves to supply ambient air preferably in parallel so as to general or allow an airflow with a sufficient volume for breathing in or inhaling through the mouthpiece 13.

If necessary the fluid 2 may also be atomized by means of a propellant gas.

Preferred ingredients and/or formulations of the preferably medicinal fluid 2 are listed in particular in WO 2009/047173 A2 which is incorporated herewith by reference. As already stated, these may be aqueous or non-aqueous solutions, mixtures, formulations containing ethanol or free from solvent, or the like.

LIST OF REFERENCE NUMERALS 1 nebulizer
2 fluid
3 container
4 bag
5 pressure generator
6 holder
7 drive spring
8 locking element
9 conveying tube
10 non-return valve
11 pressure chamber
12 nozzle
13 mouthpiece
14 aerosol
15 air supply opening
16 upper housing part
17 inner part
17a upper part of the inner part
17b lower part of the inner part
18 housing part (lower part)
19 retaining element
20 spring
21 container base
22 piercing element
23 monitoring device
24 fluid outlet
25 first closure
26 second closure
27 closure part
28 flange
29 transportation lock
30 securing member
31 latching lug
32 latching recess
33 latching arm
34 venting hole
35 securing means
36 holding element
36a end portion
37 locking element
37a end portion
37b actuation portion
38 base
39 spring portion
40 fixing portion
41 edge
42 control member
43 ring
44 ring portion
45 corrugation

What is claimed is:

1. A nebulizer (1) for a fluid (2), comprising:
an insertable container (3) containing the fluid (2);
a housing for receiving the container (3), wherein the container (3) is moveable back and forth along a longitudinal axis within the housing during conveying of the fluid (2), pressure generation and/or nebulization, where the housing includes a housing part (18); and a cage operating as a securing element (35) for holding the container (3), the cage including a plurality of holding and/or locking elements (36, 37), each having a proximal end coupled directly or indirectly to the housing part (18), an arm extending substantially parallel to the longitudinal axis, and a gripper element (36a, 37a, 37b) spaced away from the proximal end, the plurality of holding and/or locking elements (36, 37) being disposed annularly about a lower edge (41) the container (3), wherein respective lengths of the respective arms of the plurality of holding and/or locking elements (36, 37) are of a sufficient length such that the container (3): (i) is moveable back and forth along the longitudinal axis when the respective gripper elements (36a, 37a, 37b) of the holding and/or locking elements (36, 37) are not engaged with the lower edge (41) of the container (3) but the container (3) remains inseparable from the housing part (18); and (ii) is not moveable back and forth along the longitudinal axis when the respective gripper elements (36a, 37a, 37b) of the holding and/or locking elements (36, 37) are engaged with the lower edge (41) of the container (3).

2. The nebulizer according to claim 1, wherein:

the nebulizer includes a nozzle;

the housing includes a first housing part and the housing part is a second housing part releasably coupled to the first housing part in a longitudinal orientation and direction along the longitudinal axis;

the container includes a closure part having a first end located within the container and extending toward a second end at which a fluid outlet for the liquid is located, the fluid outlet being closed by a first closure located at the first end of the closure part in a delivery state of the nebulizer;

the nebulizer includes a conveying element for conveying the liquid from the container through the closure part and the fluid outlet towards the nozzle; and the cage operates in the delivery state of the nebulizer and an activated state of the nebulizer, and where in the activated state the cage operates such that: (i) the container is inseparable from the second housing part even when the first and second housing parts are separated, and (ii) the container is movable in the longitudinal direction along the longitudinal axis within the cage, wherein:

the delivery state: (i) is a state in which an end of the conveying element is disposed through the second end and within the closure part and through the fluid outlet of the container, but not piercing the first closure at the first end of the closure part, and (ii) is a state in which the nebulizer is shipped or delivered to the user, and the activated state is a state in which the end of the conveying element advances through the first closure and into communication with the liquid within the container such that the first closure and the fluid outlet are opened inside the nebulizer before or during first use of the nebulizer.

3. The nebulizer according to claim 1, wherein the holding and/or locking elements (36, 37) include holding elements (36) in which the gripper elements (36*a*) thereof engage the lower edge (41) of the container (3) from only one longitudinal direction, and include locking elements (37) in which the gripper elements (37*a*) thereof engage the lower edge (41) of the container (3) from only another direction, opposing the one longitudinal direction, such that when both the gripper elements (36*a*) of the holding elements (36) and the gripper elements (37*a*) of the locking elements (37) simultaneously engage the lower edge (41) of the container (3), the container (3) is not moveable back and forth along the longitudinal axis.

4. The nebulizer according to claim 3, wherein the locking elements (37) operate to pivot and/or flex with respect to the respective proximal ends thereof, in order to transition from a state in which both the gripper elements (36*a*) of the holding elements (36) and the gripper elements (37*a*) of the locking elements (37) simultaneously engage the lower edge (41) of the container (3), to a state in which the gripper elements (37*a*) of the locking elements (37) do not engage the lower edge (41) of the container (3), thereby releasing the container (3) and permitting the container to move back and forth along the longitudinal axis.

5. The nebulizer according to claim 1, wherein cage comprises an opening means for opening a venting hole (34) of the container (3).

6. The nebulizer according to claim 1, wherein the cage operates such that a transition from a state in which the container (3) is not moveable back and forth along the longitudinal axis when the respective gripper elements (36*a*, 37*a*, 37*b*) of the holding and/or locking elements (36, 37) are engaged with the lower edge (41) of the container (3), to a state when the container (3) is moveable back and forth along the longitudinal axis when the respective gripper elements (36*a*, 37*a*, 37*b*) of the holding and/or locking elements (36, 37) are not engaged with the lower edge (41) of the container (3) automatically when completely closing the housing.

7. The nebulizer according to claim 1, wherein the housing part (18) is replaceable together with the container (3), wherein the container (3) is inseparable from the housing part (18).

8. The nebulizer according to claim 1, wherein the cage is located in the housing part (18).

9. The nebulizer according to claim 1, wherein the container (3) is inseparable from the housing part (18) due to a corrugation (45) of the container (3).

10. The nebulizer according to claim 1, wherein the nebulizer (1) is constructed as an inhaler for medical aerosol treatment.

11. The nebulizer according to claim 1, wherein cage comprises a metal stamping part.

12. The nebulizer according to claim 1, wherein the cage consists of a single, unitary part.

13. A housing part for a nebulizer (1), comprising a housing part (18) for receiving the container (3), wherein the container (3) is moveable back and forth along a longitudinal axis within the housing during conveying of the fluid (2), pressure generation and/or nebulization, where the housing includes a housing part (18); and a cage operating as a securing element (35) for holding the container (3), the cage including a plurality of holding and/or locking elements (36, 37), each having a proximal end coupled directly or indirectly to the housing part (18), an arm extending substantially parallel to the longitudinal axis, and a gripper element (36*a*, 37*a*, 37*b*) spaced away from the proximal end, the plurality of holding and/or locking elements (36, 37) being disposed annularly about a lower edge (41) the container (3), wherein respective lengths of the respective arms of the plurality of holding and/or locking elements (36, 37) are of a sufficient length such that the container (3): (i)

is moveable back and forth along the longitudinal axis when the respective gripper elements (36a, 37a, 37b) of the holding and/or locking elements (36, 37) are not engaged with the lower edge (41) of the container (3) but the container (3) remains inseparable from the housing part (18); and (ii) is not moveable back and forth along the longitudinal axis when the respective gripper elements (36a, 37a, 37b) of the holding and/or locking elements (36, 37) are engaged with the lower edge (41) of the container (3).

14. The housing part according to claim 13, wherein cage comprises a metal stamping part.

15. The housing part according to claim 13, wherein cage is produced from sheet material by cutting and bending.

16. The housing part according to claim 13, wherein the cage consists of a single, unitary part.

17. The housing part according to claim 13, wherein the cage encompasses an end or bottom portion of the container (3).

18. The housing part according to claim 13, wherein the container (3) is inseparable from the housing part (18) due to a corrugation (45) of the container (3).

19. The housing part according to claim 13, wherein the holding and/or locking elements (36, 37) include holding elements (36) in which the gripper elements (36a) thereof engage the lower edge (41) of the container (3) from only one longitudinal direction, and include locking elements (37) in which the gripper elements (37a) thereof engage the lower edge (41) of the container (3) from only another direction, opposing the one longitudinal direction, such that when both the gripper elements (36a) of the holding elements (36) and the gripper elements (37a) of the locking elements (37) simultaneously engage the lower edge (41) of the container (3), the container (3) is not moveable back and forth along the longitudinal axis.

20. The housing part according to claim 19, wherein the holding and/or locking elements (36, 37) extend at least axially or in the direction of the movement of the container (3).

21. The housing part according to claim 19, wherein the locking elements (37) operate to pivot and/or flex with respect to the respective proximal ends thereof, in order to transition from a state in which both the gripper elements (36a) of the holding elements (36) and the gripper elements (37a) of the locking elements (37) simultaneously engage the lower edge (41) of the container (3), to a state in which the gripper elements (37a) of the locking elements (37) do not engage the lower edge (41) of the container (3), thereby releasing the container (3) and permitting the container to move back and forth along the longitudinal axis.

22. The housing part according to claim 13, wherein
the housing part includes a first housing part and a second housing part releasably coupled to the first housing part in a longitudinal orientation and direction along the longitudinal axis;
the container includes a closure part having a first end located within the container and extending toward a second end at which a fluid outlet for the liquid is located, the fluid outlet being closed by a first closure located at the first end of the closure part in a delivery state of the nebulizer;
the nebulizer includes a conveying element for conveying the liquid from the container through the closure part and the fluid outlet towards the nozzle; and
the cage operates in the delivery state of the nebulizer and an activated state of the nebulizer, and where in the activated state the cage operates such that: (i) the container is inseparable from the second housing part even when the first and second housing parts are separated, and (ii) the container is movable in the longitudinal direction along the longitudinal axis within the cage, wherein:
the delivery state: (i) is a state in which an end of the conveying element is disposed through the second end and within the closure part and through the fluid outlet of the container, but not piercing the first closure at the first end of the closure part, and (ii) is a state in which the nebulizer is shipped or delivered to the user, and
the activated state is a state in which the end of the conveying element advances through the first closure and into communication with the liquid within the container such that the first closure and the fluid outlet are opened inside the nebulizer before or during first use of the nebulizer.

23. The housing part according to claim 13, wherein cage comprises an opening means for opening a venting hole (34) of the container (3).

* * * * *